(12) United States Patent
Pei et al.

(10) Patent No.: US 10,625,079 B2
(45) Date of Patent: Apr. 21, 2020

(54) METHOD AND SYSTEM FOR MANAGING RESIDUAL CHARGE FOR MULTI-POINT PACING THERAPY

(71) Applicant: PACESETTER, INC., Sylmar, CA (US)

(72) Inventors: Xing Pei, Thousand Oaks, CA (US); Kyungmoo Ryu, Palmdale, CA (US)

(73) Assignee: Pacesetter, Inc., Sylmar, CA (US)

( * ) Notice: Subject to any disclaimer, the term of this patent is extended or adjusted under 35 U.S.C. 154(b) by 258 days.

(21) Appl. No.: 15/803,588

(22) Filed: Nov. 3, 2017

(65) Prior Publication Data
US 2019/0134399 A1    May 9, 2019

(51) Int. Cl.
| | |
|---|---|
| A61N 1/368 | (2006.01) |
| A61N 1/37 | (2006.01) |
| A61N 1/02 | (2006.01) |
| A61N 1/365 | (2006.01) |
| A61N 1/05 | (2006.01) |

(52) U.S. Cl.
CPC .......... *A61N 1/3684* (2013.01); *A61N 1/025* (2013.01); *A61N 1/3686* (2013.01); *A61N 1/36507* (2013.01); *A61N 1/36842* (2017.08); *A61N 1/3706* (2013.01); *A61N 1/3716* (2013.01); *A61N 1/056* (2013.01); *A61N 1/36843* (2017.08)

(58) Field of Classification Search
None
See application file for complete search history.

(56) References Cited

U.S. PATENT DOCUMENTS

| | | | |
|---|---|---|---|
| 4,741,342 A * | 5/1988 | Stotts | A61N 1/368 607/12 |
| 8,391,980 B2 | 3/2013 | Bornzin et al. | |
| 8,442,634 B2 | 5/2013 | Min et al. | |
| 8,923,965 B2 | 12/2014 | Min et al. | |
| 9,216,285 B1 | 12/2015 | Boling et al. | |
| 9,232,485 B2 | 1/2016 | Wu et al. | |
| 10,166,396 B2 * | 1/2019 | Schrock | A61N 1/3627 |
| 2005/0075677 A1 | 4/2005 | Ganion et al. | |
| 2006/0271120 A1 | 11/2006 | Ternes | |
| 2008/0046017 A1 | 2/2008 | Stahmann et al. | |

(Continued)

OTHER PUBLICATIONS

European Search Report dated Mar. 3, 2019; Application No. 18204012.1.

*Primary Examiner* — Kennedy Schaetzle
(74) *Attorney, Agent, or Firm* — Dean D. Small; The Small Patent Law Group, LLC

(57) ABSTRACT

Methods and systems are provided for managing residual charge for multi-point pacing therapy. The method and system provide an electrode configuration that includes an atrial (A) electrode, a right ventricular (RV) electrode and multiple left ventricular (LV) electrodes. The method and system deliver pacing pulses for an MPP therapy, during a first cardiac cycle, from a pulse generator to the electrode configurations. The pacing pulses are separated by pacing pulse (PP) intervals. The method and system dynamically adjust at least one of a timing or a duration of discharge pulses for the residual charge to form a discharge sequence. The method and system activate the discharge pulses based on the discharge sequence, during the first cardiac cycle, to the multiple LV electrodes to distribute the residual charge across the PP intervals.

20 Claims, 10 Drawing Sheets

(56) References Cited

U.S. PATENT DOCUMENTS

| | | | |
|---|---|---|---|
| 2010/0069980 A1* | 3/2010 | Stahmann | A61N 1/36185 607/5 |
| 2011/0046690 A1* | 2/2011 | Shelchuk | A61N 1/368 607/17 |
| 2014/0039333 A1 | 7/2012 | Min | |
| 2016/0228708 A1 | 8/2016 | Ternes et al. | |
| 2016/0339248 A1 | 11/2016 | Schrock et al. | |

* cited by examiner

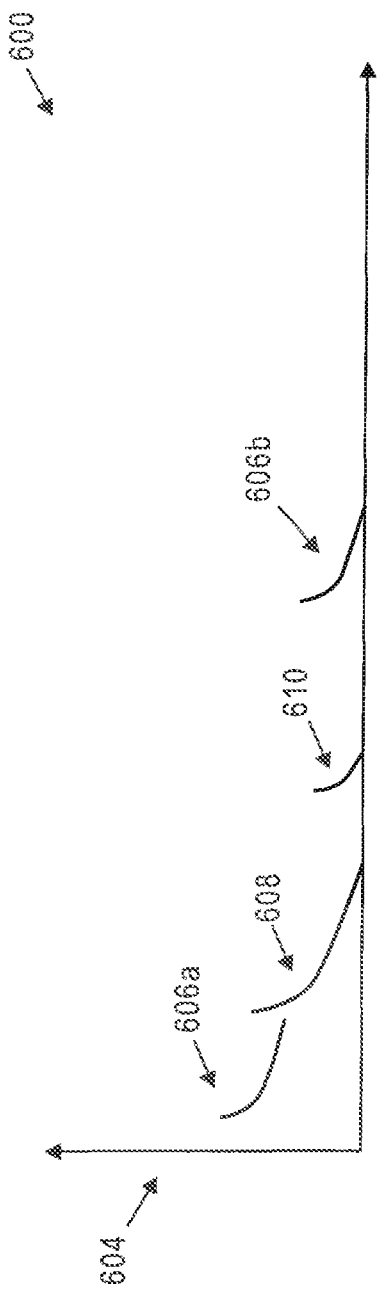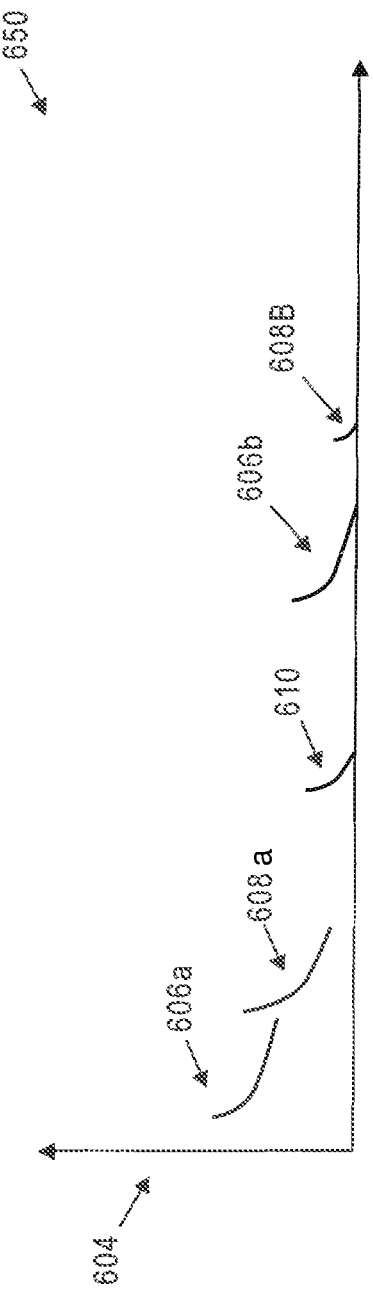

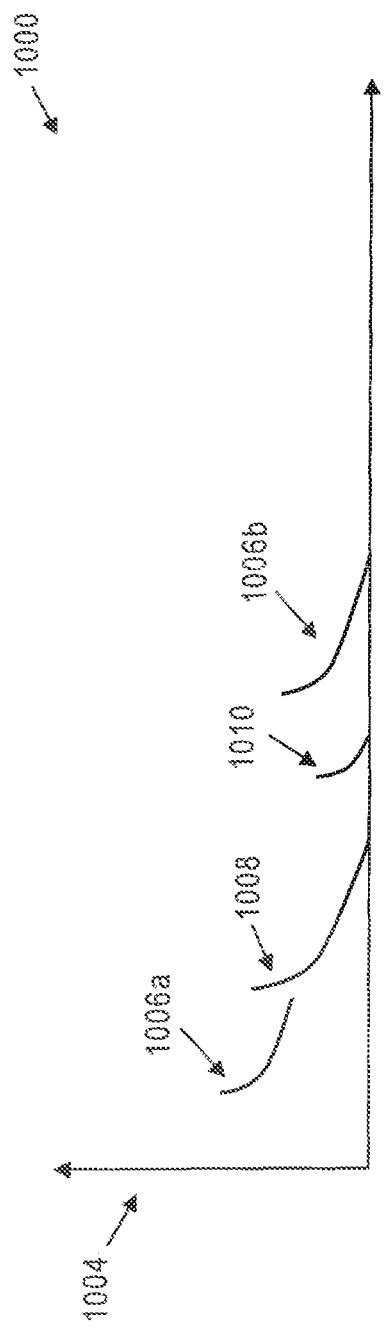
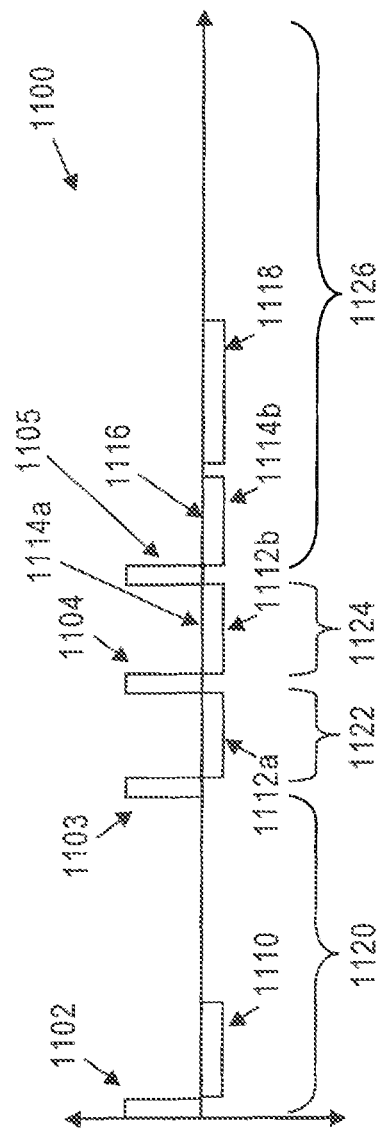
FIG. 10
FIG. 11

METHOD AND SYSTEM FOR MANAGING RESIDUAL CHARGE FOR MULTI-POINT PACING THERAPY

BACKGROUND

Embodiments of the present disclosure generally relate to methods and systems for managing residual charge for multi-point pacing therapy.

Multi-point pacing (MPP) therapy provides cardiac activation of multiple locations to achieve synchrony of heart contractions. A major challenge of MPP therapy is the charge balancing or pacing neutrality after providing pacing. Pacing neutrality is required in conventional MPP systems to eliminate the accumulated charge of pacing electrodes, and prevent the uncontrolled release of electrical charges to potentially stimulate cardiac tissue. The stimulation of cardiac tissue from accumulated charge of pacing electrodes can cause patient safety concerns when using the MPP system. Additionally, if the residual charge after pacing is not fully discharged, the residual charge may affect the ability of sensing of cardiac signals and affect the overall pacing neutrality.

Typically, after each chamber pacing or each pulse (i.e., atrial pacing, right ventricular pacing, or left ventricular pacing), the traditional implantable CRT device systems form discharge pulses immediately following each pacing pulse. The immediate discharge allows the sufficient discharge of the residual charges in the pacing system to achieve the pacing neutrality. However, in MPP systems, achieving pacing neutrality becomes challenging because of an increase number of the pulses delivered and the short time interval between the pacing pulses. Based on the shorter time intervals, less time is available to achieve pacing neutrality. For example, a duration of the discharge pulses is not enough to dissipate the residual charges. Thus, a desire remains to improve managing the residual charge for the MPP therapy.

SUMMARY

In accordance with embodiments herein, a method is provided for managing residual charge in connection with multi-point pacing (MPP). The method includes providing an electrode configuration that includes an atrial (A) electrode, a right ventricular (RV) electrode and multiple left ventricular (LV) electrodes. The method includes delivering pacing pulses for an MPP therapy, during a first cardiac cycle, from a pulse generator to the electrode configurations. The pacing pulses are separated by pacing pulse (PP) intervals. The method includes dynamically adjusting at least one of a timing or duration of discharge pulses for the residual charge to form a discharge sequence. The method includes activating the discharge pulses based on the discharge sequence, during the first cardiac cycle, to the multiple LV electrodes to distribute the residual charge across the PP intervals.

Optionally, the dynamically adjusting operation includes determining a discharge sequence based on lengths first and second PP intervals. Optionally, the dynamically adjusting operation includes selecting a discharge sequence that reduces a portion of the residual charge associated with a first pacing pulse after at least first, second, and third pacing pulses. Optionally, the discharge sequence includes at least first and second discharge pulses for the residual charge associated with a first pacing pulse. The at least first and second discharge pulses are activated during corresponding first and second PP intervals. Optionally, the delivering operation includes delivering first and second pacing pulses utilizing first and second LV electrodes. The discharge sequence includes at least first and second discharge pulses for the residual charge associated with the first pacing pulse. The at least first and second discharge pulses are activated after the first and second pacing pulses. Optionally, the discharge sequence includes at least one of a single discharge pulse, two discharge pulses, or simultaneous discharge pulses. Optionally, the method includes calculating a length of first, second, and third PP intervals based on the first cardiac cycle of a patient. The first, second, and third PP intervals are interposed between the first, second, and third pulses, respectively.

In accordance with embodiments herein, a system is provided for managing residual charge in connection with multi-point pacing (MPP). The system includes electrodes configured to be located proximate to an atrial (A) site, a right ventricular (RV) site and multiple left ventricular (LV) sites of the heart. The system includes memory to store program instructions and a one or more processors. The one or more processors is configured to implement the program instructions. Based on the program instructions, the one or more processors delivers pacing pulses for an MPP therapy, during a first cardiac cycle, from a pulse generator to the electrode configurations, the pacing pulses separated by pacing pulse (PP) intervals. The one or more processors dynamically adjust at least one of a timing or a duration of discharge pulses for the residual charge to form a discharge sequence, and activates the discharge pulses based on the discharge sequence, during the first cardiac cycle, to the multiple LV electrodes to distribute the residual charge across the PP intervals.

Optionally, the one or more processors determine a discharge sequence based on lengths first and second PP intervals. Optionally, the one or more processors select a discharge sequence that reduces a portion of the residual charge associated with a first pacing pulse after at least first, second and third pacing pulses. Optionally, the discharge sequence includes at least first and second discharge pulses for the residual charge associated with a first pacing pulse. The at least first and second discharge pulses are activated during corresponding first and second PP intervals. Optionally, the one or more processors deliver first and second pacing pulses utilizing first and second LV electrodes. Additionally or alternatively, the discharge sequence includes at least first and second discharge pulses for the residual charge associated with the first pacing pulse. The at least first and second discharge pulses are activated after the first and second pacing pulses. Optionally, the discharge sequence includes at least one of a single discharge pulse, two discharge pulses, or simultaneous discharge pulses. Optionally, the one or more processors calculate a length of first, second, and third PP intervals based on the first cardiac cycle of a patient. The first, second, and third PP intervals being interposed between the first, second, and third pulses, respectively.

In accordance with embodiments herein, a method is provided for managing residual charge in connection with multi-point pacing (MPP). The method includes providing an electrode configuration that includes an atrial (A) electrode, a right ventricular (RV) electrode and multiple left ventricular (LV) electrodes. The method includes delivering pacing pulses for an MPP therapy, during a first cardiac cycle, from a pulse generator to the electrode configurations, the pacing pulses separated by pacing pulse (PP) intervals. The method includes calculating a length of first, second, and third PP intervals based on the first cardiac cycle of a patient. The first, second, and third PP intervals are interposed between the first, second, and third pulses, respectively. The method includes dynamically adjusting at least one of a timing or a duration of discharge pulses for the residual charge to form a discharge sequence based on lengths of the first and second PP intervals. The discharge sequence includes at least one of a single discharge pulse, two discharge pulses, or simultaneous discharge pulses. The method includes activating the discharge pulses based on the discharge sequence, during the first cardiac cycle, to the multiple LV electrodes to distribute the residual charge across the PP intervals.

Optionally, the dynamically adjusting operation includes selecting a discharge sequence that reduces a portion of the residual charge associated with a first pacing pulse after at least first, second and third pacing pulses. Optionally, the discharge sequence includes at least first and second discharge pulses for the residual charge associated with a first pacing pulse. The at least first and second discharge pulses activated during corresponding first and second PP intervals. Optionally, the delivering operation comprises delivering first and second pacing pulses by utilizing the first and second LV electrodes. Additionally or alternatively, the discharge sequence includes at least first and second discharge pulses for the residual charge associated with the first pacing pulse. The at least first and second discharge pulses emitted after the first and second pacing pulses.

BRIEF DESCRIPTION OF THE DRAWINGS

FIG. 6A-B illustrate embodiments of graphical illustrations of residual charges of the discharge sequence shown in FIG. 5.

FIG. 10 illustrates an embodiment of a graphical illustration of residual charges of the discharge sequence shown in FIG. 9.

FIG. 11 illustrates an embodiment of a MPP therapy/discharge sequence.

DETAILED DESCRIPTION

Figure 1:
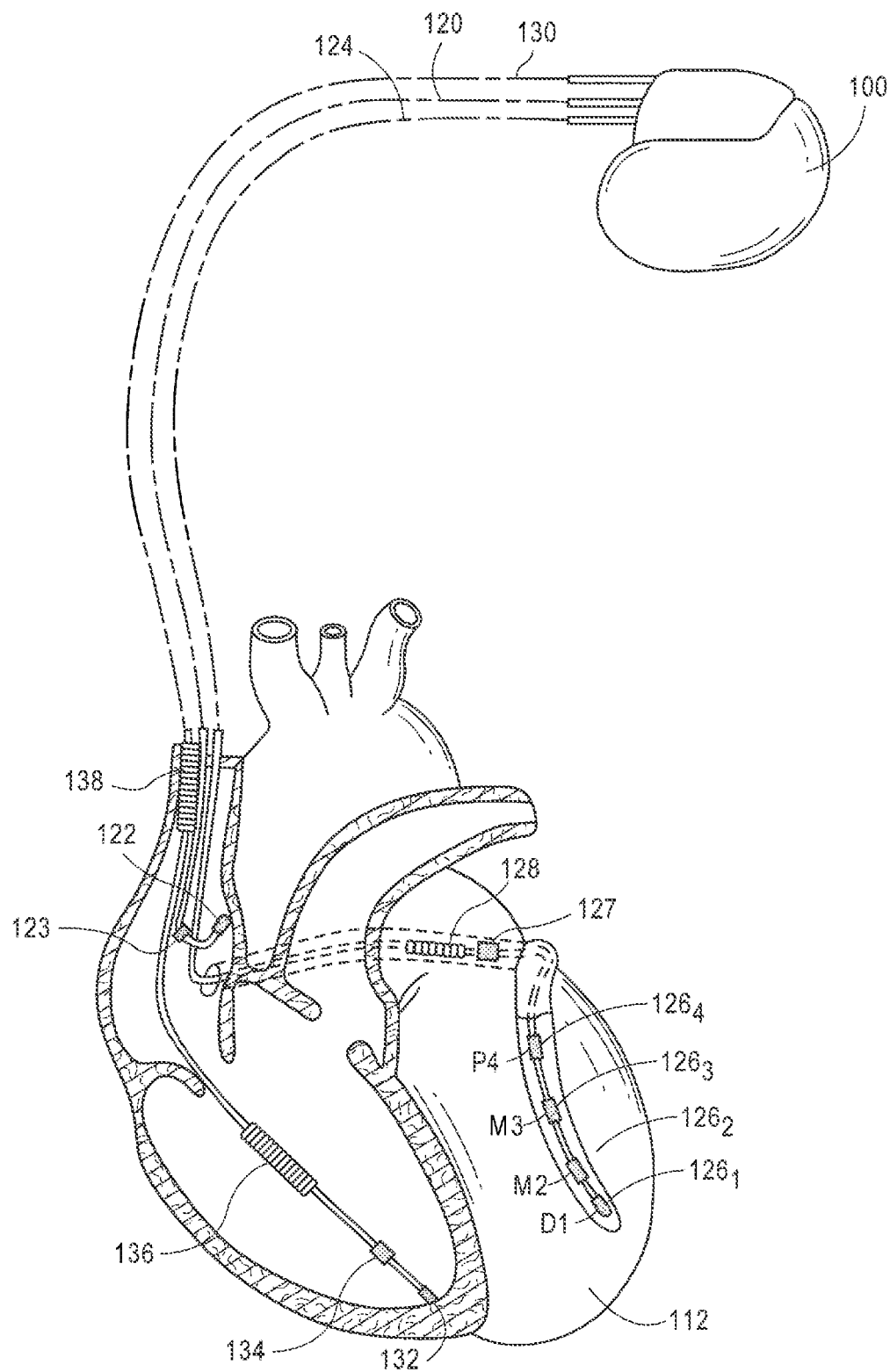
FIG. 1 illustrates an exemplary implantable medical devices (IMD) formed in accordance with embodiments herein.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

The methods described herein may employ structures or aspects of various embodiments (e.g., systems and/or methods) discussed herein. In various embodiments, certain operations may be omitted or added, certain operations may be combined, certain operations may be performed simultaneously, certain operations may be performed concurrently, certain operations may be split into multiple operations, certain operations may be performed in a different order, or certain operations or series of operations may be re-performed in an iterative fashion. It should be noted that, other methods may be used, in accordance with an embodiment herein. Further, wherein indicated, the methods may be fully or partially implemented by one or more processors of one or more devices or systems. While the operations of some methods may be described as performed by the processor(s) of one device, additionally, some or all of such operations may be performed by the processor(s) of another device described herein.

Terms

The term "pacing pulse interval" or "PP interval" refer to a time interval experienced between successive pulses or evoked responses at a site of interest in a right ventricle (RV) or a left ventricle (LV).

The term "discharge sequence" refers to a series of discharge pulses. The discharge pulses represent residual charges that are discharged during a pacing pulse interval. The discharge sequence can include a single discharge pulse, two discharge pulses, or simultaneous discharge pulses during the PP intervals.

Embodiments may be implemented in connection with one or more implantable medical devices (IMDs). Non-limiting examples of IMDs include one or more of implantable lead-based or leadless therapy devices. For example, the IMD may represent a pacemaker, cardioverter, cardiac rhythm management device, defibrillator, whether lead-based or leadless. For example, the IMD may include one or more structural and/or functional aspects of the device(s)

described in U.S. Pat. No. 9,216,285 "Leadless Implantable Medical Device Having Removable And Fixed Components"; U.S. Pat. No. 8,442,634 "Systems and Methods for Controlling Ventricular Pacing in Patients with Long Inter-Atrial Conduction Delays"; and/or U.S. Pat. No. 8,923,965 "Systems and Methods for Optimizing AV/VV Pacing Delays Using Combined IEGM/Impedance-Based Techniques for use with Implantable Medical Devices"; U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An implantable Medical Device", which are hereby incorporated by reference.

Electrode Configuration

FIG. 1 illustrates an exemplary IMD 100 formed in accordance with embodiments herein. The IMD 100 is shown in electrical communication with a heart 112 by way of a right atrial lead 120 having an atrial tip electrode 122 and an atrial ring electrode 123 implanted in the atrial appendage. The IMD 100 is also in electrical communication with the heart 112 by way of a right ventricular lead 130 having, in this embodiment, a ventricular tip electrode 132, a right ventricular ring electrode 134, a right ventricular (RV) coil electrode 136, and a superior vena cava (SVC) coil electrode 138. Typically, the right ventricular lead 130 is transvenously inserted into the heart so as to place the RV coil electrode 136 in the right ventricular apex, and the SVC coil electrode 138 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, IMD 100 is coupled to a multi-pole LV lead 124 designed for placement in the "CS region" via the CS OS for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 124 is designed to receive atrial and ventricular cardiac signals and to deliver left ventricular pacing therapy using a set of four left ventricular electrodes $126_1$, $126_2$, $126_3$, and $126_4$, also referred to as a proximal LV electrode, a $Mid_1$ LV electrode, a $Mid_2$ LV electrode and a distal LV electrode, respectively. For example, the LV electrodes $126_1$-$126_4$ may be provided on a quadripole lead for left atrial pacing therapy. Shocking therapy may utilize at least a left atrial coil electrode 128 and/or a left atrial ring electrode 127 implanted on or near the left atrium. In other examples, more or fewer LV electrodes are provided. Although only three leads are shown, it should be understood that additional leads (with one or more pacing, sensing and/or shocking electrodes) might be used and/or additional electrodes might be provided on the leads already shown, such as additional electrodes on the RV lead.

Implantable Medical Device

Figure 2:
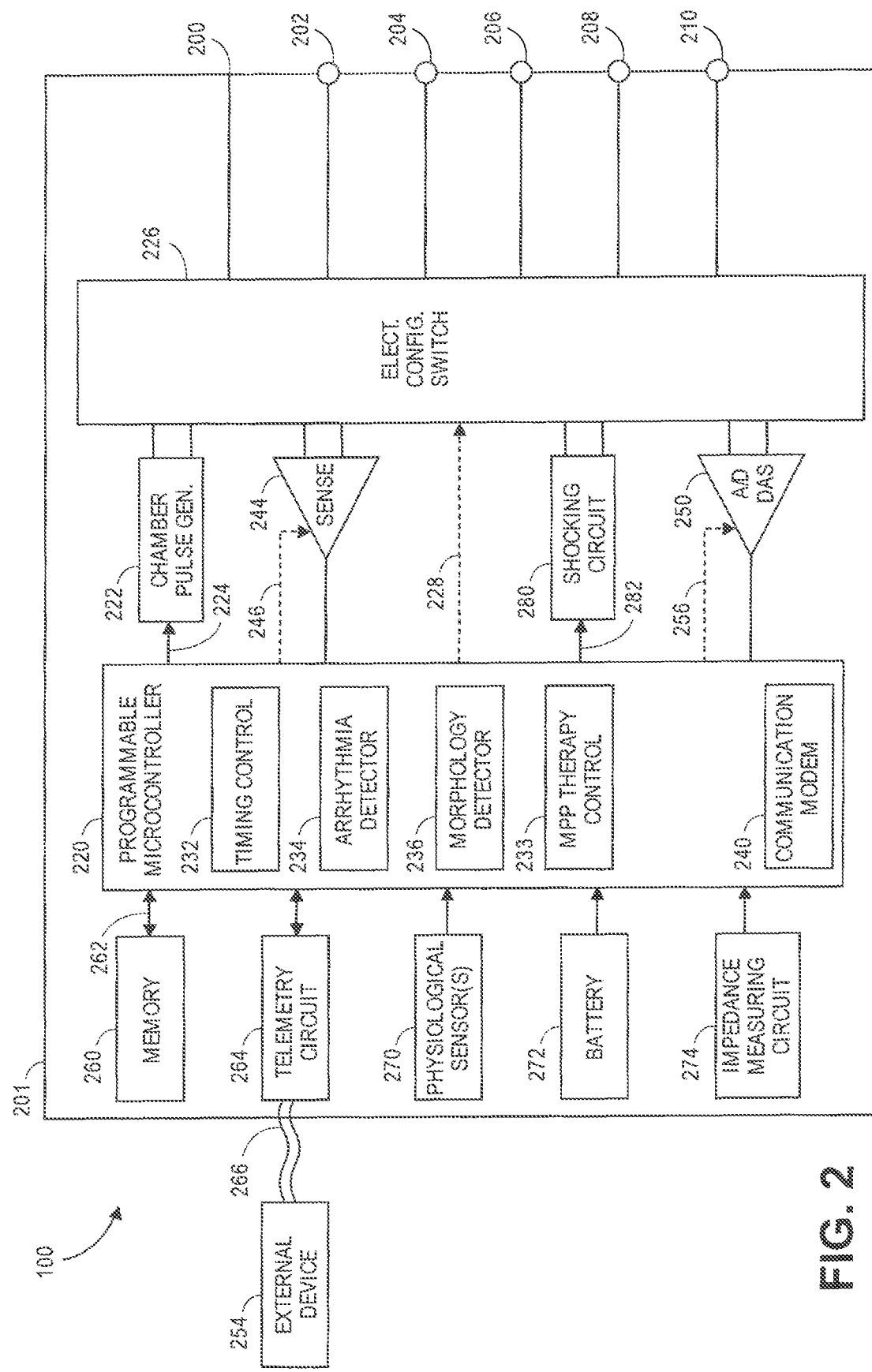
FIG. 2 shows a block diagram of an exemplary IMD that is implanted into the patient as part of the implantable cardiac system in accordance with embodiments herein.

FIG. 2 shows a block diagram of an exemplary IMD 100 that is implanted into the patient as part of the implantable cardiac system. The IMD 100 may be implemented as a full-function biventricular pacemaker, equipped with both atrial and ventricular sensing and pacing circuitry for four chamber sensing and stimulation therapy (including both pacing and shock treatment). Optionally, the IMD 100 may provide full-function cardiac resynchronization therapy. Alternatively, the IMD 100 may be implemented with a reduced set of functions and components.

The IMD 100 has a housing 201 to hold the electronic/computing components. The housing 201 (which is often referred to as the "can", "case", "encasing", or "case electrode") may be programmably selected to act as the return electrode for certain stimulus modes. Housing 201 further includes a connector (not shown) with a plurality of terminals, a portion of which are designated as terminals electrically coupled to electrodes 202, 204, 206, 208, and 210. The terminals may be connected to electrodes that are located in various locations within and about the heart. For example, the terminals may include: a terminal to be coupled to a first electrode (e.g., a tip electrode) 202 located in a first chamber; a terminal to be coupled to a second electrode (e.g., tip electrode) 204 located in a second chamber, a terminal to be coupled to an electrode (e.g., ring) 206 located in the first chamber; a terminal to be coupled to an electrode located (e.g., ring electrode) 208 in the second chamber; and a terminal to be coupled to an electrode (e.g., coil) 210 located in the SVC. The type and location of each electrode may vary. For example, the electrodes may include various combinations of ring, tip, coil and shocking electrodes and the like. It is understood that more or fewer terminals may be utilized. With reference to FIG. 1, the housing 201 includes at least a number of terminals corresponding to the number of electrodes provided on leads 120, 124 and 130. For example, terminals are provided to connect to the LV electrodes $126_1$-$126_4$.

The IMD 100 includes a programmable microcontroller 220 that controls various operations of the IMD 100, including cardiac monitoring and stimulation therapy. The programmable microcontroller 220 may include one or more processors. Optionally, the programmable microcontroller 220 may include a central processing unit (CPU), one or more microprocessors, or any other electronic component capable of processing inputted data according to specific logical instructions. Optionally, the programmable microcontroller 220 may include and/or represent one or more hardware circuits or circuitry that include, are connected with, or that both include and are connected with one or more processors, controllers, and/or other hardware logic-based devices. Additionally or alternatively, the programmable microcontroller 220 may execute instructions stored on a tangible and non-transitory computer readable medium (e.g., the memory 260). The programmable microcontroller 220 may include RAM and/or ROM memory, logic and timing circuitry, state machine circuitry, and I/O circuitry.

The IMD 100 further includes one or more pulse generators 222 that generates stimulation pulses for delivery by one or more electrodes coupled thereto. The pulse generator 222 is controlled by the microcontroller 220 via control signal 224. The pulse generator 222 is coupled to the select electrode(s) via an electrode configuration switch 226, which includes multiple switches for connecting the desired electrodes to the appropriate I/O circuits, thereby facilitating electrode programmability. The switch 226 is controlled by a control signal 228 from the microcontroller 220.

In the example of FIG. 2, a single pulse generator 222 is illustrated. Optionally, the IMD 100 may include multiple pulse generators, similar to pulse generator 222, where each pulse generator is coupled to one or more electrodes and controlled by the microcontroller 220 to deliver select stimulus pulse(s) to the corresponding one or more electrodes.

The microcontroller 220 is illustrated to include timing control circuitry 232 to control the timing of the stimulation pulses. The timing control circuitry 232 may also be used for the timing of refractory periods, blanking intervals, noise detection windows, evoked response windows, alert intervals, marker channel timing, PP intervals, and/or the like. The microcontroller 220 also has an arrhythmia detector 234 for detecting arrhythmia conditions and a morphology detector 236 to review and analyze one or more features of the morphology of cardiac signals.

The microcontroller 220 includes MPP therapy control circuitry 233 to implement the processes described herein for controlling MPP pacing therapy adjusted for pacing latency and including/excluding certain LV sites. The MPP therapy control circuitry 233 manages a pacing therapy that utilizes left ventricular MPP, based on the VV delays for the corresponding LV sites.

The microcontroller 220 may select one of the discharge sequences stored in the memory 260. The discharge sequences define when a series of discharge pulses are emitted by the microcontroller 220. The discharge pulses are configured to discharge a residual charge stored in a coupling capacitor 324 during one or more PP intervals.

Figure 3:
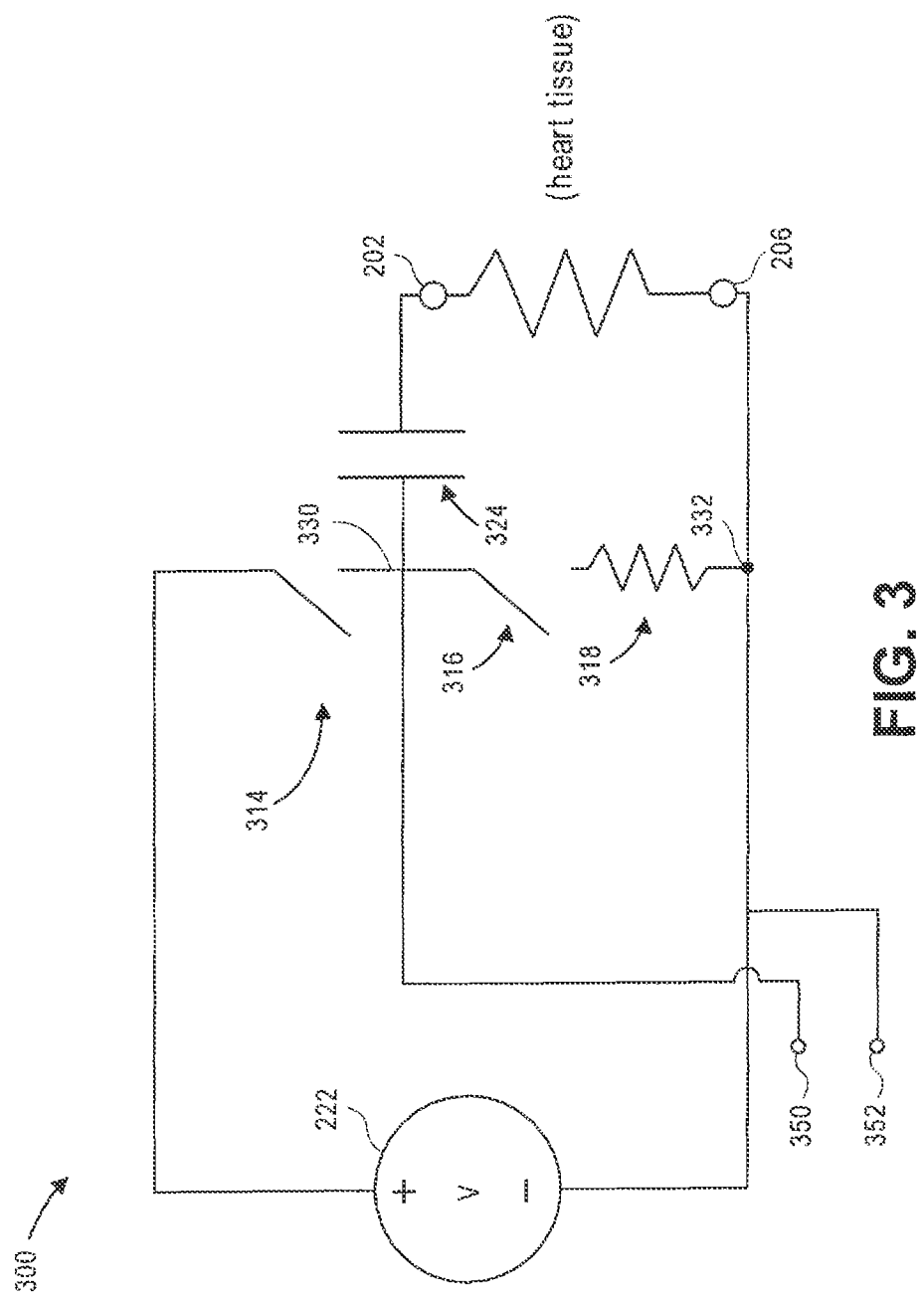
FIG. 3 illustrates an embodiment of a schematic representation of a portion of an electrode configuration switch within the IMD.

FIG. 3 illustrates an embodiment 300 of a schematic representation of a portion of the electrode configuration switch 226 within the IMD 100. The electrode configuration switch 226 is electrically coupled to the pulse generator 222. The electrode configuration switch 226 includes a pacing switch 314 and a discharge switch 316. A node 330 is interposed between the pacing switch 314 and the discharge switch 316. The node 330 is electrically connected to the electrode 202 (e.g., the tip electrode) that is provided at a desired stimulus site proximate to the heart 112. The node 332 is positioned on an opposite side of the discharge switch 316, which is coupled to the pulse generator 222, a resistor 318, and the electrode 206 (e.g., the ring electrode). The electrode 206 is also located at a desired stimulus site proximate to the heart 112. In various embodiments, the electrodes 202, 204, 206, 208, 210 may be coupled to additional pacing switches 314, discharge switches 316, coupling capacitors 324, resistors 318, and/or the like. For example, the electrode configuration switch 226 includes a plurality of pacing switches 314, discharge switches 316, coupling capacitors 324, resistors 318, and/or the like forming a switch matrix. The switch matrix enables the microcontroller 220 to deliver paces and/or discharge pulses to the different electrodes 200, 202, 204, 206, 208, 210 of the IMD 100.

During a pacing operation, the pacing switch 314 is closed, while the discharge switch 316 is held open. The pacing pulse can range from 2-5 volts. The pacing stimulus is delivered from the pulse generator 222 to the electrodes 202, 206, which induces a voltage differential between the electrodes 202, 206 stimulating the chamber. When the pacing operation is completed, the microcontroller 220 instructs the pacing switch 314 to open.

A coupling capacitor 324 is provided between the node 330 and the electrode 202. The coupling capacitor 324 may be approximately 0.5 microfarads. Additionally or alternatively, the electrical characteristics of the coupling capacitor 324 may be based on a desired shape of the pacing pulse. For example, the coupling capacitor 324 is configured to form a shape (e.g., morphology, slope) of the pacing pulse. Additionally, the coupling capacitor 324 is provided to separate the power supply stage (e.g., voltage provided by the pulse generator 222) from the electrode stage (e.g., generally including the electrodes 202, 204, 206, 208, 210). The coupling capacitor 324 is used to filter noise and undesirable signals from passing between the pulse generator 222 and the electrode 202.

The resistor 318 is provided between nodes 330, 332, which is in series with the discharge switch 316. The resistor 318 may be approximately 40 Ohms. Optionally, the electrical characteristics of the resistor 318 may be adjusted to adjust a length of the discharge pulse. For example, the impedance of the resistor 318 can be increased and/or decreased to adjust a length of the discharge pulse to achieve pacing neutrality.

For example, during the pacing operation, initially, the coupling capacitor 324 holds a zero charge potential. The pacing switch 314 is closed by the configuration switch 226. The coupling capacitor 324 instantaneously becomes a low resistance path that couples the positive voltage potential (e.g., V) from the power generator 222 to the electrode 202. The coupling capacitor 324 then begins to build up a—voltage potential. Across the electrodes 202, 206 a pacing pulse is delivered to the heart 112 (e.g., heart tissue). For example, the heart 112 is represented in FIG. 3 as a resistor between the electrodes 202, 206, which is indicative of the heart tissue.

The microcontroller 220 selects a discharge sequence based on lengths of the PP intervals between the pacing operations delivered to the electrodes 200, 202, 204, 206, 208, 210, during the cardiac cycle. The discharge sequence can include discharge pulses subsequent to the pacing operation of a pair of electrodes (e.g., the electrodes 202, 206), during multiple PP intervals, simultaneously with multiple pairs of electrodes, and/or the like.

For example, the discharge pulse is initiated by the microcontroller 220 by opening the pacing switch 314. The coupling capacitor 324 continues to have a positive voltage potential. The microcontroller 220 discharges the coupling capacitor 324 to remove the residual charge of the coupling capacitor 324. The microcontroller 220 forms the discharge pulse by closing the discharge switch 316. For example, when the discharge switch 316 is closed the voltage at the node 330 and the residual charge of the coupling capacitor 324 is discharged through the resistor 318. It may be noted that the amount of charge held in the coupling capacitor 324 during the pacing operation is below the levels needed to achieve a pulse to the heart 112. For example, the discharge pulse may extend approximately 15 milliseconds and have an amplitude of a few hundred millivolts. The discharge pulse does not interfere with the normal physiologic behavior sought to be achieved through the pacing operation of the IMD 100. The microcontroller 220 closes the discharge switch 316 based on the discharge sequence stored in the memory 260.

Additionally or alternatively, the microcontroller 220 can monitor the residual charge of the coupling capacitor 324. For example, the microcontroller 220 monitors a voltage potential across terminals 350, 352. The terminal 350 is coupled to the node 330 (e.g., which is electrically coupled to the electrode 202) and the terminal 352 is coupled to the ground or common of the power generator 222. The microcontroller 220 determines a voltage potential across the coupling capacitor 324 by identifying a voltage across the terminals 350, 352. Based on the voltage across the terminals 350, 352, the microcontroller 220 determines whether the coupling capacitors 324 have a residual charge. For example, the microcontroller 220 compares the voltage across the terminals 350, 352 to a predetermined threshold. The predetermined threshold represents the ground and/or common voltage of the power generator 222. When the voltage across the terminals 350, 352 is above the predetermined threshold, the microcontroller 220 may extend the discharge pulse and/or deliver a subsequent discharge pule during an alternative PP interval. Optionally, when the voltage across the terminal 350, 352 is below the predetermined threshold, the microcontroller 220 may shorten the discharge pulse. For example, the microcontroller 220 instructs the switch 226 to open the discharge switch 316 when the voltage is at the predetermined threshold.

Returning to FIG. 2, although not shown, the microcontroller 220 may further include other dedicated circuitry and/or firmware/software components that assist in monitoring various conditions of the patient's heart and managing pacing therapies.

The IMD 100 is further equipped with a communication modem (modulator/demodulator) 240 to enable wireless communication with other devices, implanted devices and/or external devices. In one implementation, the communication modem 240 may use high frequency modulation of a signal transmitted between a pair of electrodes. As one example, the signals may be transmitted in a high frequency range of approximately 10-80 kHz, as such signals travel through the body tissue and fluids without stimulating the heart or being felt by the patient.

The communication modem 240 may be implemented in hardware as part of the microcontroller 220, or as software/firmware instructions programmed into and executed by the microcontroller 220. Alternatively, the modem 240 may reside separately from the microcontroller as a standalone component.

The IMD 100 includes sensing circuitry 244 selectively coupled to one or more electrodes that perform sensing operations, through the switch 226 to detect the presence of cardiac activity in the right chambers of the heart. The sensing circuitry 244 may include dedicated sense amplifiers, multiplexed amplifiers, or shared amplifiers. It may further employ one or more low power, precision amplifiers with programmable gain and/or automatic gain control, bandpass filtering, and threshold detection circuit to selectively sense the cardiac signal of interest. The output of the sensing circuitry 244 is connected to the microcontroller 220 which, in turn, triggers or inhibits the pulse generator 222 in response to the absence or presence of cardiac activity. The sensing circuitry 244 receives a control signal 246 from the microcontroller 220 for purposes of controlling the gain, threshold, polarization charge removal circuitry (not shown), and the timing of any blocking circuitry (not shown) coupled to the inputs of the sensing circuitry.

The IMD 100 further includes an analog-to-digital (A/D) data acquisition system (DAS) 250 coupled to one or more electrodes via the switch 226 to sample cardiac signals across any pair of desired electrodes. The data acquisition system 250 is configured to acquire intracardiac electrogram signals, convert the raw analog data into digital data, and store the digital data for later processing and/or telemetric transmission to an external device 254 (e.g., a programmer, local transceiver, or a diagnostic system analyzer). The data acquisition system 250 is controlled by a control signal 256 from the microcontroller 220.

The microcontroller 220 is coupled to a memory 260 by a suitable data/address bus 262. The programmable operating parameters used by the microcontroller 220 are stored in memory 260 and used to customize the operation of the IMD 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart within each respective tier of therapy.

The operating parameters of the IMD 100 may be non-invasively programmed into the memory 260 through a telemetry circuit 264 in telemetric communication via communication link 266 with the external device 254. The telemetry circuit 264 allows intracardiac electrograms and status information relating to the operation of the IMD 100 (as contained in the microcontroller 220 or memory 260) to be sent to the external device 254 through the established communication link 266.

The IMD 100 can further include one or more physiologic sensors 270. Such sensors are commonly referred to as "rate-responsive" sensors because they are typically used to adjust pacing stimulation rates according to the exercise state of the patient. However, the physiological sensor 270 may further be used to detect changes in cardiac output, changes in the physiological condition of the heart, or diurnal changes in activity (e.g., detecting sleep and wake states). Signals generated by the physiological sensors 270 are passed to the microcontroller 220 for analysis.

A battery 272 provides operating power to all of the components in the IMD 100. The battery 272 is capable of operating at low current drains for long periods of time, and is capable of providing high-current pulses (for capacitor charging) when the patient requires a shock pulse (e.g., in excess of 2 A, at voltages above 2 V, for periods of 10 seconds or more). The battery 272 also desirably has a predictable discharge characteristic so that elective replacement time can be detected. As one example, the battery 272 employs lithium/silver vanadium oxide batteries.

The IMD 100 further includes an impedance measuring circuit 274 that is enabled by the microcontroller 220 via a control signal 282. As explained herein, the impedance measuring circuit 274 may be utilized in a feedback loop to collect cardiogenic impedance signals along one or more impedance vectors while delivering an MPP pacing therapy. For example, the cardiogenic impedance signals may be collected as described in U.S. Pat. No. 8,923,965 "Systems and Methods for Optimizing AV/VV Pacing Delays Using Combined IEGM/Impedance-Based Techniques for use with Implantable Medical Devices"; and U.S. Patent Application Publication 2014/0039333 "Systems and Methods for Detecting Mechanical Dyssynchrony and Stroke Volume for use with an Implantable Medical Device Employing a Multi-Pole Left Ventricular Lead", which are incorporated herein by reference in their entirety.

The IMD 100 can be operated as an implantable cardioverter/defibrillator (ICD) device, which detects the occurrence of an arrhythmia and automatically applies an appropriate electrical shock therapy to the heart aimed at terminating the detected arrhythmia. To this end, the microcontroller 220 further controls a shocking circuit 280 by way of a control signal 282. The shocking circuit 280 generates shocking pulses of low (e.g., up to 0.5 joules), moderate (e.g., 0.5-10 joules), or high energy (e.g., 211 to 40 joules), as controlled by the microcontroller 220. Such shocking pulses are applied to the patient's heart through shocking electrodes. It is noted that the shock therapy circuitry is optional and may not be implemented in the IMD, as the various slave pacing units described below will typically not be configured to deliver high voltage shock pulses. On the other hand, it should be recognized that the slave pacing unit can be used within a system that includes backup shock capabilities, and hence such shock therapy circuitry may be included in the IMD.

Managing Residual Charge

Figure 4:
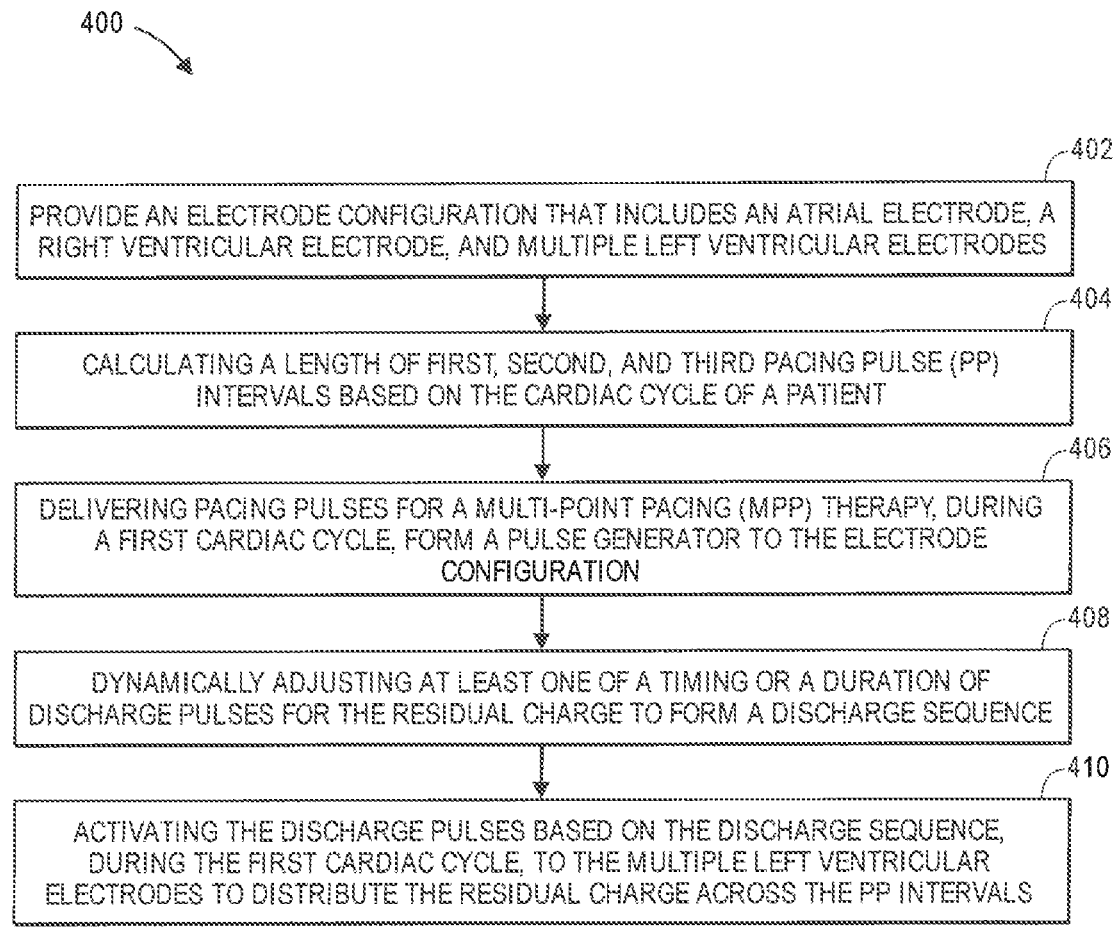
FIG. 4 illustrates a method for managing a residual charge in connection with multi-point pacing therapy, in accordance with embodiments herein.

FIG. 4 illustrates a method 400 for managing a residual charge in connection with MPP therapy, in accordance with embodiments herein. The method 400, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 400 may be used as one or more algorithms to direct hardware to perform one or more operations described herein. Optionally, the operations of FIG. 4 may be implemented in combination with the systems and methods described in U.S. Pat. Nos. 8,442,634; 8,923,965 and/or U.S. Patent Application Publication 2014/0039333.

Beginning at 402, an electrode configuration is provided that includes an atrial (A) electrode, a right ventricular (RV) electrode, and multiple left ventricular (LV) electrodes. The IMD 100 is coupled to one or more leads that include the A electrodes, the RV electrode, and multiple LV electrodes in connection with FIG. 1. For example, the IMD 100 is shown in electrical communication with the heart 112 by way of the right atrial lead 120 having the A tip electrode 122 and the A ring electrode 123. The IMD 100 is shown in electrical communication with the heart 112 by way of the RV lead 130 having the ventricular tip electrode 132, the RV ring electrode 134, and the RV coil electrode 136. Additionally, the IMD 100 is coupled to the multiple LV lead 124. The multiple LV lead 124 includes a set of four LV electrodes 126$_1$, 126$_2$, 126$_3$, and 126$_4$ (e.g., referred to as a proximal LV electrode, a Mid$_1$ LV electrode, a Mid$_2$ LV electrode and a distal LV electrode, respectively).

At 404, the one or more processors calculate a length of first, second, and/or third PP intervals based on the first cardiac cycle of the patient. The first, second, and third pacing pulses are separated by PP intervals, which are interposed between the first, second, and third pacing pulses. For example, the first PP interval is interposed between the first and second pacing pulse, the second PP interval is interposed between the second and third pacing pulses, and the third PP interval is subsequent to the third pacing pulse. The lengths of the PP intervals are based on the first cardiac cycle calculated by the one or more processors.

At 406, the one or more processors (e.g., of the microcontroller 220) deliver pacing pulses for the MPP therapy, during a first cardiac cycle, from the pulse generator 222 to the electrode configuration. For example, the one or more processors calculate the first cardiac cycle based on measurements of the sensing circuitry 244 and/or the physiological sensor 270. The one or more processors measure the cardiac activity based on measurements of the sensing circuitry 244. For example, the sensing circuitry 244 measures impedances from the RV electrodes (e.g., the RV coil electrode 136) and the electrodes of the multiple LV lead 124. Additionally or alternatively, the one or more processors may adjust the first cardiac cycle based on measurements from the physiological sensor 270. For example, the physiological sensor 270 detects physiological parameters of the patient indicative of exercise, sleeping, and/or the like. The one or more processors adjust the relative timings of the first cardiac cycle based on the physiological parameters. For example, the one or more processors reduce the rate of the pacing pulses, for the first cardiac cycle when the physiological parameters measured by the physiological sensor 270 indicates the patient is exercising.

Based on the first cardiac cycle, the one or more processors deliver the pacing pulses for the MPP therapy. The first cardiac cycle defines when the IMD 100 delivers pacing pulses to corresponding portions of the heart 112. For example, the one or more processors instruct the electrode configuration switch 226 via the control signal 228 to deliver the pacing pulses. The control signal 228 configures the switch 226 to couple the electrodes 202, 204, 206, 208, 210 to the pulse generator 222 and to deliver the pacing pulses to the A electrode, the RV electrode, and the multiple LV electrodes. For example, the one or more processors deliver a first pulse to a first set of LV electrodes, a second pulse to a second set of LV electrodes, and a third pulse to the RV electrode.

At 408, the one or more processors dynamically adjusting at least one of a timing or a duration of discharge pulses for the residual charge to form a discharge sequence. For example, based on lengths of the PP intervals between the MPP therapy pacing pulses the one or more processors select a MPP therapy/discharge sequence 500, 700, 900, 1100. The MPP therapy/discharge sequences 500, 700, 900, 1100 shift a position and/or duration of the discharge pulses based on the lengths of the PP intervals.

At 410, the one or more processors activate the discharge pulses (e.g., the discharge pulses 512*a-b,* 514, 516, 518, 712*a-b,* 714, 716, 718, 912*a-b,* 914, 916, 918, 1112*a-b,* 1114*a-b,* 1116, 1118) based on the discharge sequence, during the first cardiac cycle. For example, the one or more processors close the discharge switches 316 based on the discharge pulses 512*a-b,* 514, 516, 518, 712*a-b,* 714, 716, 718, 912*a-b,* 914, 916, 918, 1112*a-b,* 1114*a-b,* 1116, 1118 of the selected MPP therapy/discharge sequence 500, 700, 900, 1100 at 408.

FIGS. 5, 7, 9, and 11 illustrate different MPP therapy/discharge sequences 500, 700, 900, 1100 that include therapy pulses (associated with the MPP therapy) and residual discharge pulses. The MPP therapy/discharge sequences 500, 700, 900, 1100 may be stored in the memory 260. The one or more processors select one of the MPP therapy/discharge sequences 500, 700, 900, 1100 based on the lengths of the MPP therapy, which has different lengths of first, second, and/or third PP intervals. The MPP therapy/discharge sequences 500, 700, 900, 1100 include different timing and/or durations for discharge pulses, which dissipate the residual charges on the coupling capacitors 324 of the switch 226. For example, the one or more processors dynamically adjust a timing and/or duration of the discharge pulses for the residual charge by selecting one of the MPP therapy/discharge sequences based on the lengths of the PP intervals. The MPP therapy/discharge sequences 500, 700, 900, 1100 includes at least one of a single discharge pulse, two discharge pulses, or simultaneous discharge pulses.

Figure 5:
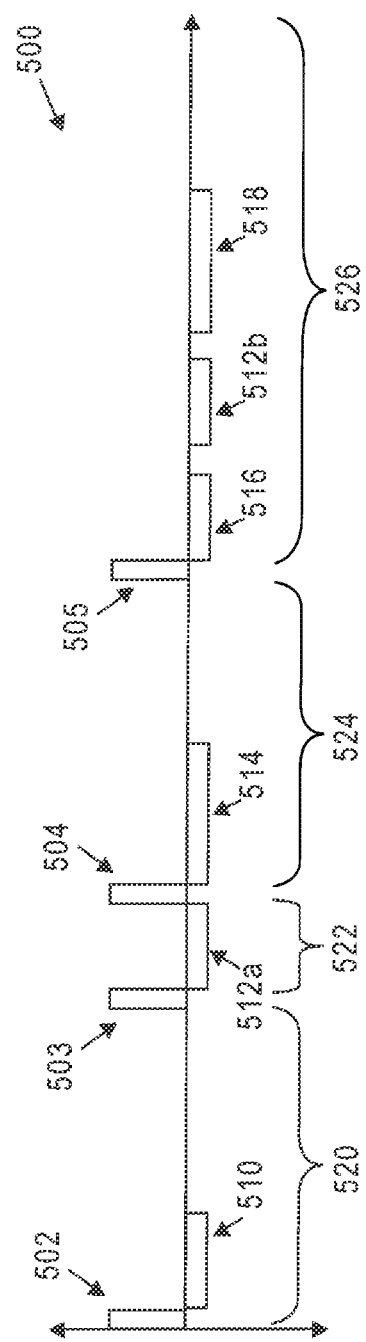
FIG. 5 illustrates an embodiment of a MPP therapy/discharge sequence.

FIG. 5 illustrates an embodiment of the MPP therapy/discharge sequence 500. The discharge sequence 500 includes a series of consecutive pulses 502-505 that are delivered during one cardiac cycle (e.g., the first cardiac cycle). The discharge sequence 500 includes an A pulse 502 delivered to the atrial electrode (e.g., the A tip electrode 122, the A ring electrode 123), a first pulse 503 delivered to a first set of LV electrodes, a second pulse 504 delivered to a second set of LV electrodes, and a third pulse 505 delivered to the RV electrode, all during the first cardiac cycle. The pulses 502-505 are separated by PP intervals 520, 522, 524, 526, all during one cardiac cycle. The PP interval 520 separates the A pulse 502 and the first pulse 503. The PP interval 522 separates the first and second pulses 503, 504. The PP interval 524 separates the second and third pulses 504, 505. The PP interval 526 is subsequent to the third pulse 505.

The MPP therapy/discharge sequence 500 also include one or more discharge pulses 510, 512a-b, 514, 516, 518 that are emitted during the PP intervals 520, 522, 524, 526. A duration and/or timing of the discharge pulses 510, 512a-b, 514, 516, 518 are defined by the discharge sequence. For example, the PP interval 526 includes a plurality of successive discharge pulses 516, 512b, 518.

The A pulse 502 is emitted by the one or more processors. For example, the one or more processors instruct the switch 226 to close the pacing switch 314, which couples the A electrodes to the pulse generator 222. Subsequent to the delivery of the A pulse 502, the one or more processors instruct the switch 226 to open the pacing switch 314 and close the discharge switch 316 to form the discharge pulse 510. When the discharge switch 316 is closed, the residual charge of the coupling capacitor 324 from the A pulse 502 is dissipated through the resistor 318. In the present example, a duration of the PP interval 520 is over 16 milliseconds based on the first cardiac cycle. Based on the duration of the PP interval 520, sufficient time is afforded for the one or more processors to dissipate all of the residual charge associated with the A pulse 502 of the discharge pulse 510.

Next, the first pulse 503 is delivered after the PP interval 520 following the A pulse 502. The first pulse 503 represents a pacing pulse discharged through the first set of LV electrodes. Subsequent to the delivery of the first pulse 503, the one or more processors instruct the switch 226 to open the pacing switch 314 and closes the discharge switch 316 to form the discharge pulse 512a. In the present example, a duration of the PP interval 522 is less than 10 milliseconds based on the first cardiac cycle. The duration of the PP interval 522 is not sufficient to allow time for the one or more processors to dissipate all of the residual charge associated with the first pulse 504 through the discharge pulse 512a. For example, the PP interval 522 is shortened based on a timing of the second pulse 504 for the MPP therapy, and thus all of the residual charge associated with the first pulse 503 cannot be dissipated. The discharge pulse 512a represents a partial discharge of the residual charge of the coupling capacitor 324. To dissipate the rest of the residual charge, a secondary discharge pulse (e.g., the discharge pulse 512b) is needed to discharge a remainder of the residual charge on the coupling capacitor 324 during an alternative PP interval (e.g., the PP interval 526).

Next, the second pulse 504 is delivered after the PP interval 522 following the first pulse 503. The second pulse 504 represents a pacing pulse discharged through the second set of LV electrodes. Subsequent to the delivery of the second pulse 504, the one or more processors instruct the switch 226 to open the pacing switch 314 and close the discharge switch 316 to form the discharge pulse 514. When the discharge switch 316 is closed, the residual charge of the coupling capacitor 324 associated with the second pulse 504 is dissipated through the resistor 318. In the present example, a duration of the PP interval 524 is over 20 milliseconds based on the first cardiac cycle. The duration of the PP interval 524 affords sufficient time for the one or more processors to dissipate all of the residual charge associated with the second pulse 504 as the discharge pulse 514.

Next, the third pulse 505 is delivered after the PP interval 524 following the second pulse 504. The third pulse 505 represents a pacing pulse discharged through the RV electrodes. Subsequent to the delivery of the third pulse 505, the one or more processors instruct the switch 226 to open the pacing switch 314 and close the discharge switch 316 to form the discharge pulse 514. When the discharge switch 316 is closed, the residual charge of the coupling capacitor 324 associated with the third pulse 505 is dissipated through the resistor 318. In the present example, a duration of the PP interval 526 is over 20 milliseconds based on the first cardiac cycle and a subsequent cardiac cycle (e.g., a second cardiac cycle). The duration of the PP interval 526 affords sufficient time for the one or more processors to dissipate all of the residual charge associated with the third pulse 505 of the discharge pulse 516.

Additionally, the PP interval 526 can include a plurality of successive discharge pulses 516, 512b, 518. For example, during the PP interval 526 the one or more processors form discharge pulses 516, 512b, 518 associated with alternative pulses. Subsequent to the discharge pule 516, the one or more processors initiates the discharge pulse 512b to dissipate the remaining residual charge of the coupling capacitor 324 associated with the first pulse 503. The MPP therapy/discharge sequence 500 reduces a portion of the residual charge 512a-b associated with the first pacing pulse 503 after at least the first pacing pulse 503 and the third pacing pulse 505.

The discharge pulse 518 is used by the one or more processors to dissipate any remaining residual charges associated with the pulses 502-505. For example, the one or more processors may compare the residual charges of the coupling capacitors 324 associated with the pulses 502-505 with the predetermined threshold. The one or more processors compare the residual charges of the coupling capacitors 324 with the predetermined threshold to identify discharge pulses that have not discharged the residual charges corresponding to the discharge pulses 510, 512a-b, 514, 516. The identified residual charges are dissipated by the one or more processors through the discharge pulse 518.

FIGS. 6A-B are graphical representations 600, 650 of the residual charges 606a-b, 608, 610 on the coupling capacitors 324 associated with the pulses 502-505. The residual charges 606a-b, 608, 610 are shown dissipated via the discharge pulses 510, 512a-b, 514, 516 over time.

FIG. 6A illustrates an embodiment of a graphical illustration 600 of the residual charges 606a-b, 608, 610 for the MPP therapy/discharge sequence 500, shown in FIG. 5. The residual charges 606a-b, 608, 610 are plotted with a horizontal axes 602 representing time and a vertical axis 604 representing a voltage across the coupling capacitor 324. The residual charges 606a, 608, 610, 606b sequentially correspond to the PP intervals 522, 524, 526, respectively, in FIG. 5.

For example, the residual charges 606a-b represents the voltage remaining across the coupling capacitor 324 after the first pulse 503. A decrease in the residual charge 606a occurs as the discharge pulse 512a is delivered. For example, during the PP interval 522 the one or more processors instruct the switch 226 to close the discharge switch 316. The discharge pulse 512a extends for the length of the PP interval 522, but is terminated before discharging all of the residual charge. In connection with FIG. 6A, the residual charge 606a is not completely dissipated through the resistor 318. For example, the one or more processors compare the residual charge 606a with the predetermined threshold. Based on a difference between the residual charge 606a and the predetermined threshold, the one or more processors determine that additional residual charge remains on the coupling capacitor 324 (e.g., the additional residual charge 606b). The predetermined threshold may correspond to the horizontal axis 602 representing the common and/or ground of the pulse generator 222. As explained before, the additional residual charge 606b is emitted later during the discharge pulse 512b.

The residual charge 608 represents the voltage across the coupling capacitor 324 from the second pulse 504. A decrease in the residual charge 608 is based on the discharge pulse 514. The discharge pulse 514 extends for a portion of the PP interval 524. For example, the one or more processors instruct the switch 226 to close the discharge switch 316. As the residual charge 608 is dissipated through the resistor 318, the one or more processors compare the residual charge 608 with the predetermined threshold. During the duration of the discharge pulse 514, the residual charge 608 reaches the predetermined threshold. For example, the one or more processors determine that the residual charge 608 is at the predetermined threshold. The one or more processors instruct the switch 226 to open the discharge switch 316 when the residual charge 608 is at the predetermined threshold.

The residual charge 610 represents the voltage across the coupling capacitor 324 from the third pulse 505. The decrease in the residual charge 610 is based on the discharge pulse 516. The discharge pulse 516 extends for a portion of the PP interval 526. For example, the one or more processors instruct the switch 226 to close the discharge switch 316. As the residual charge 610 is dissipated through the resistor 318, the one or more processors compare the residual charge 610 with the predetermined threshold. During the duration of the discharge pulse 516, the residual charge 610 reaches the predetermined threshold. For example, the one or more processors determine that the residual charge 610 is at the predetermined threshold. The one or more processors instructs the switch 226 to open the discharge switch 316 when the residual charge 608 is at the predetermined threshold.

The length and/or duration of the PP interval 526 enables multiple discharge pulses 516, 512b, 518 to occur during the PP interval 526. For example, based on the length of the PP interval 526, the one or more processors reduces a portion of the residual charge 606a-b after the first pulse 503 and the third pulse 504. The discharge pulse 512b is configured to dissipate a remaining portion of the residual charge 606a shown as the additional residual charge 606b. For example, the discharge pulse 512b is configured to dissipate the residual charge 606b. The one or more processors instruct the switch 226 to close the discharge switch 316 based on the first pulse 503. As the residual charge 606b is dissipated through the resistor 318, the one or more processors compare the residual charge 606b with the predetermined threshold. During the duration of the discharge pulse 512b, the residual charge 606b reaches the predetermined threshold. The residual charges 606a-b from the first pulse 503 are emitted during different PP intervals 522, 526. When the one or more processors determine that the residual charge 606b is at the predetermined threshold, the one or more processors instruct the switch 226 to open the discharge switch 316.

The discharge pulse 518 is utilized by the one or more processors to dissipate any remaining residual charges from the first, second, and/or third pulses 503-505. FIG. 6B illustrates an embodiment of a graphical illustration 650 of the residual charges 606a-b, 608a-b, 610 of the MPP therapy/discharge sequence 500 shown in FIG. 5. For example, the duration of the discharge pulse 514, represented as the residual charge 608a, is not dissipated during the discharge pulse 514. The one or more processors compare the residual charge 608a with the predetermined threshold, and determines that the residual charge 608a remains on the coupling capacitor 324. The one or more processors dissipate the remaining residual charge 608b during the discharge pulse 518.

Figure 7:
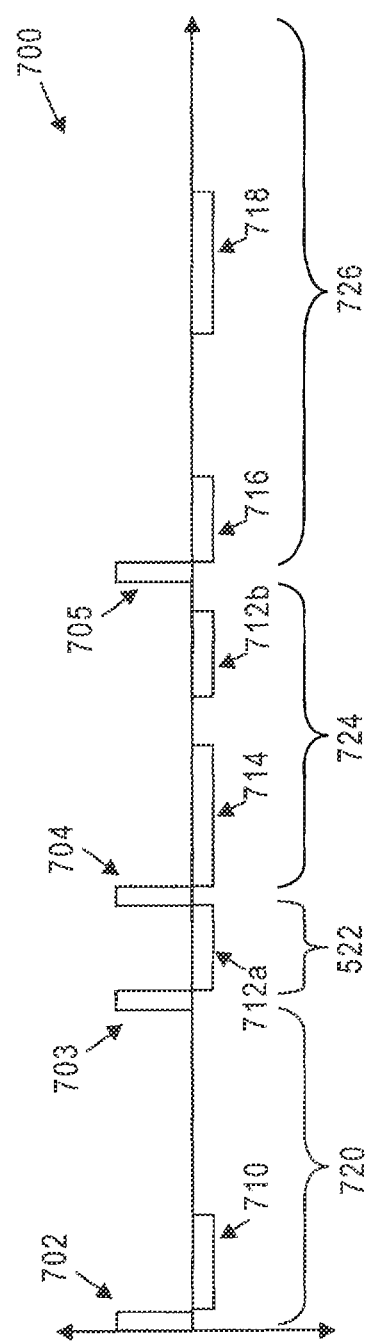
FIG. 7 illustrates an embodiment of a MPP therapy/discharge sequence.

FIG. 7 illustrates an embodiment of the MPP therapy/discharge sequence 700. The MPP therapy/discharge sequence 700 includes a series of consecutive pulses 702-705 that are delivered during one cardiac cycle (e.g., the first cardiac cycle). The MPP therapy/discharge sequence 700 includes an A pulse 702 delivered to the A electrode, a first pulse 703 delivered to the first set of LV electrodes, a second pulse 704 delivered to the second set of LV electrodes, and a third pulse 705 delivered to the RV electrode, all during the first cardiac cycle. The pulses 702-705 are separated by PP intervals 720, 722, 724, 726, all during one cardiac cycle. The PP interval 720 separates the A pulse 702 and the first pulse 703. The PP interval 722 separates the first pulse 703 and the second pulse 704. The PP interval 724 separates the second pulse 704 and the third pulse 705. The PP interval 726 is subsequent to the third pulse 705.

The MPP therapy/discharge sequence 700 includes one or more discharge pulses 710, 712a-b, 714, 716, 718 that are emitted during the PP intervals 720, 722, 724, 726. A duration and/or timing of the discharge pulses 710, 712a-b, 714, 716, 718 are defined by the MPP therapy/discharge sequence 700. In the present example, the PP interval 720 has a length that is over 16 milliseconds. The duration of the PP interval 720 is sufficient to allow time for the one or more processors to dissipate all of the residual charge associated with the A pulse 702. In the present example, the PP interval 722 has a length that is less than 10 milliseconds. The duration of the PP interval 722 is not sufficient to allow time for the one or more processors to dissipate all of the residual charge associated with the first pulse 703. The discharge pulse 712a is a partial discharge of the residual charge associated with the first pulse 703. To dissipate the rest of the residual charge, a secondary discharge pulse (e.g., the discharge pulse 712b) is needed to discharge the remainder of the residual charge during a later PP interval (e.g., the PP interval 724).

The MPP therapy/discharge sequence 700 includes an adjusted PP interval 724. For example, the length of the PP interval 724 is longer relative to the PP interval 524 (FIG. 5). In the present example, a duration of the PP interval 724 is over 24 milliseconds based on the first cardiac cycle. Based on the difference in lengths of the PP intervals 524, 724, the one or more processors can position multiple successive discharge pulses 714, 712b associated with the first and second pulses 703-704, respectively. For example, the one or more processors shift a timing of the discharge pulse 712b to occur subsequent to the discharge pulse 714. The MPP therapy/discharge sequence 700 reduces a portion of the residual charge 712a-b associated with the first pacing pulse 703 after at least the first pacing pulse 703 and the second pacing pulse 704. For example, the MPP therapy/discharge sequence 700 activates the first and second discharge pulses 712a-b, 714 during the first and second PP intervals 722, 724.

In the present example, the PP interval 726 has a length that is over 20 milliseconds. The duration of the PP interval 726 is sufficient to allow time for the one or more processors to dissipate all of the residual charge associated with the third pulse 705. Additionally, the PP interval 726 can include a plurality of successive discharge pulses 716, 718. For example, during the PP interval 726 the one or more processors form the discharge pulse 716 associated with the third pulse 705. Optionally, the PP interval 726 includes the discharge pulse 718, which is used by the one or more processors to dissipate any remaining residual charges associated with the pulses 702-705. For example, the one or more processors may compare the residual charges of the coupling capacitors 324 associated with the pulses 702-705 with the predetermined threshold. The one or more processors compare the residual charges of the coupling capacitors 324 with the predetermined threshold to identify discharge pulses that have not discharged the residual charges corresponding to the discharge pulses 710, 712a-b, 714, 716. The identified residual charges are dissipated by the one or more processors through the discharge pulse 718.

Figure 8:
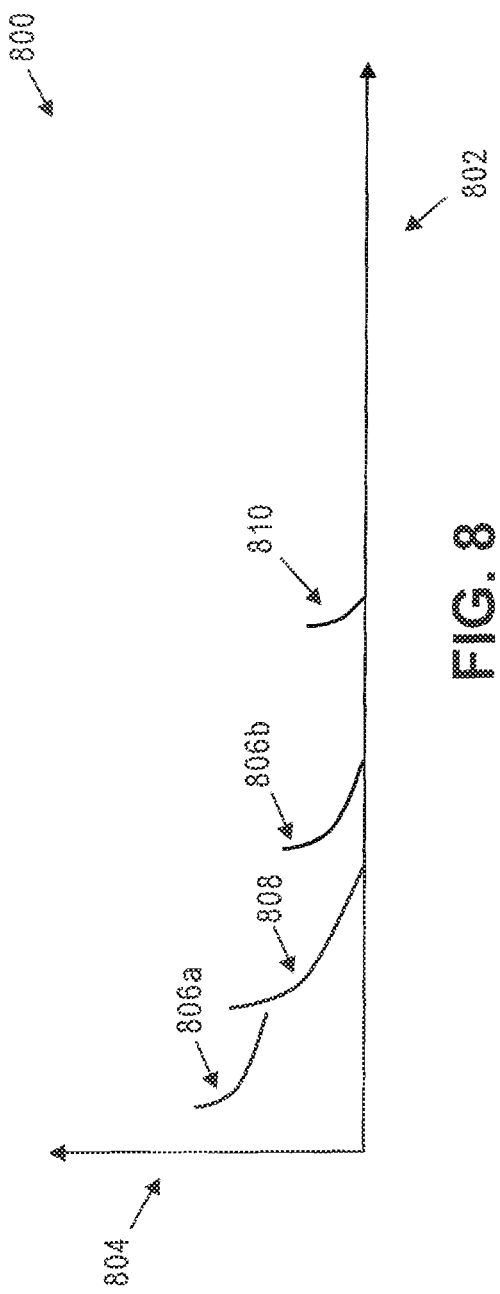
FIG. 8 illustrates an embodiment of a graphical illustration of residual charges of the discharge sequence shown in FIG. 7.

FIG. 8 illustrates an embodiment of a graphical illustration 800 of residual charges 806a-b, 808, 810 of the MPP therapy/discharge sequence 700. The residual charges 806a-b, 808, 810 are plotted with a horizontal axes 802 representing time and a vertical axis 804 representing a voltage across the coupling capacitors 324. The residual charges 806a-b, 808, 810 are shown sequentially corresponding to the PP intervals 722, 724, 726, in FIG. 7.

For example, the residual charges 806a-b represent the voltage remaining across the coupling capacitor 324 after the first pulse 703. A decrease in the residual charge 806a occurs as the discharge pulse 712a is delivered. For example, during the PP interval 722 the one or more processors instruct the switch 226 to close the discharge switch 316. The discharge pulse 712a extends for the length of the PP interval 722, but is terminated before discharging all of the residual charge. The residual charge 806a is not completely dissipated through the resistor 318. For example, the one or more processors compare the residual charge 806a with the predetermined threshold. Based on a difference between the residual charge 806a and the predetermined threshold, the one or more processors determine that additional residual charge remains on the coupling capacitor 324 (e.g., the additional residual charge 806b). The predetermined threshold may correspond to the horizontal axis 802 representing the common and/or ground of the pulse generator 222. As explained before, the additional residual charge 806b is emitted later during the discharge pulse 712b.

The residual charge 808 represents the voltage across the coupling capacitor 324 from the second pulse 704. A decrease in the residual charge 808 is based on the discharge pulse 714. The discharge pulse 714 extends for a portion of the PP interval 724. For example, the one or more processors instruct the switch 226 to close the discharge switch 316. As the residual charge 808 is dissipated through the resistor 318, the one or more processors compare the residual charge 808 with the predetermined threshold. During the duration of the discharge pulse 714, the residual charge 808 reaches the predetermined threshold. For example, the one or more processors determine that the residual charge 808 is at the predetermined threshold. The one or more processors instruct the switch 226 to open the discharge switch 316 when the residual charge 808 is at the predetermined threshold.

The length and/or duration of the PP interval 724 enables multiple discharge pulses 714, 712b to occur during the PP interval 724. For example, subsequent to the discharge of the residual charge 808, the one or more processors discharge the remaining residual charge (e.g., the residual charge 806b) associated with the first pulse 703. For example, the one or more processors instruct the switch 226 to close the discharge switch 316. As the residual charge 806b is dissipated through the resistor 318, the one or more processors compare the residual charge 806b with the predetermined threshold. During the duration of the discharge pulse 712b, the residual charge 806b reaches the predetermined threshold. For example, the one or more processors determine that the residual charge 806b is at the predetermined threshold. The one or more processors instructs the switch 226 to open the discharge switch 316 when the residual charge 806b is at the predetermined threshold.

The residual charge 810 represents the voltage across the coupling capacitor 324 associated with the third pulse 705. The decrease in the residual charge 810 is based on the discharge pulse 716. The discharge pulse 716 extends for a portion of the PP interval 726. For example, the one or more processors instruct the switch 226 to close the discharge switch 316. As the residual charge 810 is dissipated through the resistor 318, the one or more processors compare the residual charge 810 with the predetermined threshold. During the duration of the discharge pulse 716, the residual charge 810 reaches the predetermined threshold. For example, the one or more processors determine that the residual charge 810 is at the predetermined threshold. The one or more processors instructs the switch 226 to open the discharge switch 316 when the residual charge 608 is at the predetermined threshold. The one or more processors identifies any residual charges 806a-b, 808, 810 remaining on the coupling capacitors 324. Based on a difference between the residual charges 806a-b, 808, 810 and the predetermined threshold, the one or more processors dissipate the remaining residual charge during the discharge pulse 718.

Figure 9:
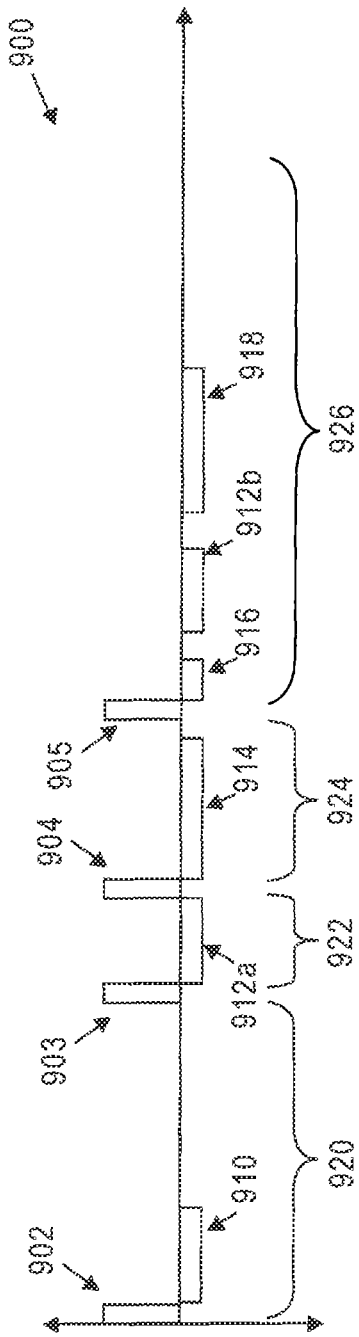
FIG. 9 illustrates an embodiment of a MPP therapy/discharge sequence.

FIG. 9 illustrates an embodiment of the MPP therapy/discharge sequence 900. The MPP therapy/discharge sequence 900 includes a series of consecutive pulses 902-905 that are delivered during one cardiac cycle (e.g., the first cardiac cycle). The MPP therapy/discharge sequence 900 includes an A pulse 902 delivered to the A electrode, a first pulse 903 delivered to the first set of LV electrodes, a second pulse 904 delivered to the second set of LV electrodes, and a third pulse 905 delivered to the RV electrode, all during the first cardiac cycle. The pulses 902-905 are separated by PP intervals 920, 922, 924, 926, all during one cardiac cycle. The PP interval 920 separates the A pulse 902 and the first pulse 903. The PP interval 922 separates the first pulse 903 and the second pulse 904. The PP interval 924 separates the second pulse 904 and the third pulse 905. The PP interval 926 is subsequent to the third pulse 905.

The MPP therapy/discharge sequence 900 includes one or more discharge pulses 910, 912a-b, 914, 916, 918 that are emitted during the PP intervals 920, 922, 924, 926. A duration and/or timing of the discharge pulses 910, 912a-b, 914, 916, 918 are defined by the MPP therapy/discharge sequence 900. In the present example, the PP interval 920 has a length that is over 16 milliseconds. The duration of the PP interval 920 is sufficient to allow time for the one or more processors to dissipate all of the residual charge associated with the A pulse 902. In the present example, the PP interval 922 has a length that is less than 10 milliseconds. The duration of the PP interval 922 is not sufficient to allow time for the one or more processors to dissipate all of the residual charge associated with the first pulse 903. The discharge pulse 912a is a partial discharge of the residual charge associated with the first pulse 903. To dissipate the rest of the residual charge, a secondary discharge pulse (e.g., the discharge pulse 912b) is needed to discharge the remainder of the residual charge during a later PP interval (e.g., the PP interval 926). In the present example, the PP interval 924 is approximately 16 milliseconds. For example, the duration of the PP interval 924 is less than the PP intervals 724 (FIG. 7), 524 (FIG. 5). The duration of the PP interval 924 is sufficient to allow time for the one or more processors to dissipate all of the residual charge associated with the second pulse 904.

In the present example, the PP interval 926 has a length that is over 20 milliseconds. The duration of the discharge pulse 916 is shorter relative to the discharge pulses 716 (FIG. 7), 516 (FIG. 5). The reduction of the discharge pulse 916 is based on a reduced amplitude and/or duration of the third pulse 905. For example, the residual charge of the coupling capacitor 324 associated with the third pulse 905 is reduced relative to the residual charges 810 (FIG. 8), 610 (FIG. 6A). Based on the reduced residual charge, the duration of the discharge pulse 916 is reduced. The duration of the PP interval 926 is sufficient to allow time for the one or more processors to dissipate all of the residual charge associated with the third pulse 905. Additionally, the PP interval 926 can include a plurality of successive discharge pulses 916, 912b, 918. For example, during the PP interval 926 the one or more processors form discharge pulses 916 associated with the third pulse 905. During the PP interval 926 the one or more processors form discharge pulses 916, 912b, 918 associated with alternatively pulses. Subsequent to the discharge pule 916, the one or more processors initiates the discharge pulse 912b to dissipate the remaining residual charge of the coupling capacitor 324 associated with the first pulse 903. Optionally, the PP interval 926 includes the discharge pulse 918, which is used by the one or more processors to dissipate any remaining residual charges associated with the pulses 902-905. For example, the one or more processors may compare the residual charges of the coupling capacitors 324 associated with the pulses 902-905 with the predetermined threshold. The one or more processors compare the residual charges of the coupling capacitors 324 with the predetermined threshold to identify discharge pulses that have not discharged the residual charges corresponding to the discharge pulses 910, 912a-b, 914, 916. The identified residual charges are dissipated by the one or more processors through the discharge pulse 918.

FIG. 10 illustrates an embodiment of a graphical illustration 1000 of residual charges 1006a-b, 1008, 1010 of the MPP therapy/discharge sequence 900. The residual charges 1006a-b, 1008, 1010 are plotted with a horizontal axes 1002 representing time and a vertical axis 1004 representing a voltage across the coupling capacitors 324. The residual charges 1006a-b, 1008, 1010 are shown sequentially corresponding to the PP intervals 922, 924, 926, shown in FIG. 9.

For example, the residual charges 1006a-b represent the voltage remaining across the coupling capacitor 324 after the first pulse 903. A decrease in the residual charge 1006a occurs as the discharge pulse 912a is delivered. For example, during the PP interval 922 the one or more processors instruct the switch 226 to close the discharge switch 316. The discharge pulse 912a extends for the length of the PP interval 922, but is terminated before discharging all of the residual charge. The residual charge 1006a is not completely dissipated through the resistor 318. For example, the one or more processors compare the residual charge 1006a with the predetermined threshold. Based on a difference between the residual charge 1006a and the predetermined threshold, the one or more processors determine that additional residual charge remains on the coupling capacitor 324 (e.g., the additional residual charge 1006b). The predetermined threshold may correspond to the horizontal axis 1002 representing the common and/or ground of the pulse generator 222. As explained before, the additional residual charge 1006b is emitted later during the discharge pulse 912b.

The residual charge 1008 represents the voltage across the coupling capacitor 324 from the second pulse 904. A decrease in the residual charge 1008 is based on the discharge pulse 914. The discharge pulse 914 extends for a portion of the PP interval 924. For example, the one or more processors instruct the switch 226 to close the discharge switch 316. As the residual charge 1008 is dissipated through the resistor 318, the one or more processors compare the residual charge 1008 with the predetermined threshold. During the duration of the discharge pulse 914, the residual charge 1008 reaches the predetermined threshold. For example, the one or more processors determine that the residual charge 1008 is at the predetermined threshold. The one or more processors instruct the switch 226 to open the discharge switch 316 when the residual charge 1008 is at the predetermined threshold.

The residual charge 1010 represents the voltage across the coupling capacitor 324 associated with the third pulse 905. The decrease in the residual charge 1010 is based on the discharge pulse 916. The discharge pulse 916 extends for a portion of the PP interval 926. For example, the one or more processors instruct the switch 226 to close the discharge switch 316. As the residual charge 1010 is dissipated through the resistor 318, the one or more processors compare the residual charge 1010 with the predetermined threshold. During the duration of the discharge pulse 916, the residual charge 1010 reaches the predetermined threshold. For example, the one or more processors determine that the residual charge 1010 is at the predetermined threshold. The one or more processors instructs the switch 226 to open the discharge switch 316 when the residual charge 1010 is at the predetermined threshold.

The length and/or duration of the PP interval 926 enables multiple discharge pulses 916, 912b, 918 to occur during the PP interval 926. For example, based on the length of the PP interval 926, the one or more processors reduces a portion of the residual charge 1006a-b after the first pulse 903 and the third pulse 904. The discharge pulse 912b is configured to dissipate a remaining portion of the residual charge 1006a shown as the additional residual charge 1006b. For example, the discharge pulse 912b is configured to dissipate the residual charge 1006b. The one or more processors instruct the switch 226 to close the discharge switch 316 based on the first pulse 903. As the residual charge 1006b is dissipated through the resistor 318, the one or more processors compare the residual charge 1006b with the predetermined threshold. During the duration of the discharge pulse 912b, the residual charge 1006b reaches the predetermined threshold. The residual charges 1006a-b from the first pulse 903 are emitted during different PP intervals 922, 926. When the one or more processors determine that the residual charge 1006b is at the predetermined threshold, the one or more processors instruct the switch 226 to open the discharge switch 316. Optionally, the one or more processors identifies any residual charges 1006a-b, 1008, 1010 remaining on the coupling capacitors 324. Based on a difference between the residual charges 1006a-b, 1008, 1010 and the predetermined threshold, the one or more processors dissipate the remaining residual charge during the discharge pulse 918.

FIG. 11 illustrates an embodiment of the MPP therapy/discharge sequence 1100. The discharge sequence 1100 shifts the timing of the discharge pulses 1112a-b, 1114a-b, 1116, 1118. For example, the discharge sequence 1100 includes discharge pulses 1112b, 1114a and 1114b, 1116 to occur simultaneously. The MPP therapy/discharge sequence 1100 includes an A pulse 1102 delivered to the A electrode, a first pulse 1103 delivered to the first set of LV electrodes, a second pulse 1104 delivered to the second set of LV electrodes, and a third pulse 1105 delivered to the RV electrode, all during the first cardiac cycle. The pulses 1102-1105 are separated by PP intervals 1120, 1122, 1124, 1126, all during one cardiac cycle. The PP interval 1120 separates the A pulse 1102 and the first pulse 1103. The PP interval 1122 separates the first pulse 1103 and the second pulse 1104. The PP interval 1124 separates the second pulse 1104 and the third pulse 1105. The PP interval 1126 is subsequent to the third pulse 1105.

The MPP therapy/discharge sequence 1100 includes one or more discharge pulses 1110, 1112a-b, 1114, 1116, 1118 that are emitted during the PP intervals 1120, 1122, 1124, 1126. A duration and/or timing of the discharge pulses 1110, 1112a-b, 1114, 1116, 1118 are defined by the MPP therapy/discharge sequence 1100. In the present example, the PP interval 1120 has a length that is over 16 milliseconds. The duration of the PP interval 1120 is sufficient to allow time for the one or more processors to dissipate all of the residual charge associated with the A pulse 1102. In the present example, the PP interval 1122 has a length that is less than 10 milliseconds. The duration of the PP interval 1122 is not sufficient to allow time for the one or more processors to dissipate all of the residual charge associated with the first pulse 1103. The discharge pulse 1112a is a partial discharge of the residual charge associated with the first pulse 1103. To dissipate the rest of the residual charge, a secondary discharge pulse (e.g., the discharge pulse 1112b) is needed to discharge the remainder of the residual charge during a later PP interval (e.g., the PP interval 1124).

In the present example, the PP interval 1124 is approximately 10 milliseconds. The one or more processors instructs the switch 226 to close the discharge switches 316 concurrently and/or simultaneously that are associated with the first and second pulses 1103, 1104. For example, the closing of the discharge switches 316 associated with the first and second pulses 1103, 1104 form the discharge pulses 1112b, 1114a that occur during the PP interval 1124. The duration of the PP interval 1122 is not sufficient to allow time for the one or more processors to dissipate all of the residual charge associated with the second pulse 1104. The discharge pulse 1114a is a partial discharge of the residual charge associated with the second pulse 1103. To dissipate the rest of the residual charge, a secondary discharge pulse (e.g., the discharge pulse 1114b) is needed to discharge the remainder of the residual charge during a later PP interval (e.g., the PP interval 1126).

In the present example, the PP interval 1126 is more than 20 milliseconds. The one or more processors instructs the switch 226 to close the discharge switches 316 concurrently and/or simultaneously that are associated with the second and third pulses 1104, 1105. For example, the closing of the discharge switches 316 associated with the second and third pulses 1104, 1105 form the discharge pulses 1114a, 1116 that occur during the PP interval 1126. The duration of the PP interval 1126 is sufficient to allow time for the one or more processors to dissipate all of the residual charge associated with the remainder of the residual charge of the second pulse 1104 and the third pulse 1105.

Optionally, the PP interval 1126 includes the discharge pulse 1118, which is used by the one or more processors to dissipate any remaining residual charges associated with the pulses 1102-1105. For example, the one or more processors may compare the residual charges of the coupling capacitors 324 associated with the pulses 702-705 with the predetermined threshold. The one or more processors compare the residual charges of the coupling capacitors 324 with the predetermined threshold to identify discharge pulses that have not discharged the residual charges corresponding to the discharge pulses 1110, 1112a-b, 1114a-b, 1116. The identified residual charges are dissipated by the one or more processors through the discharge pulse 1118.

Figure 12:
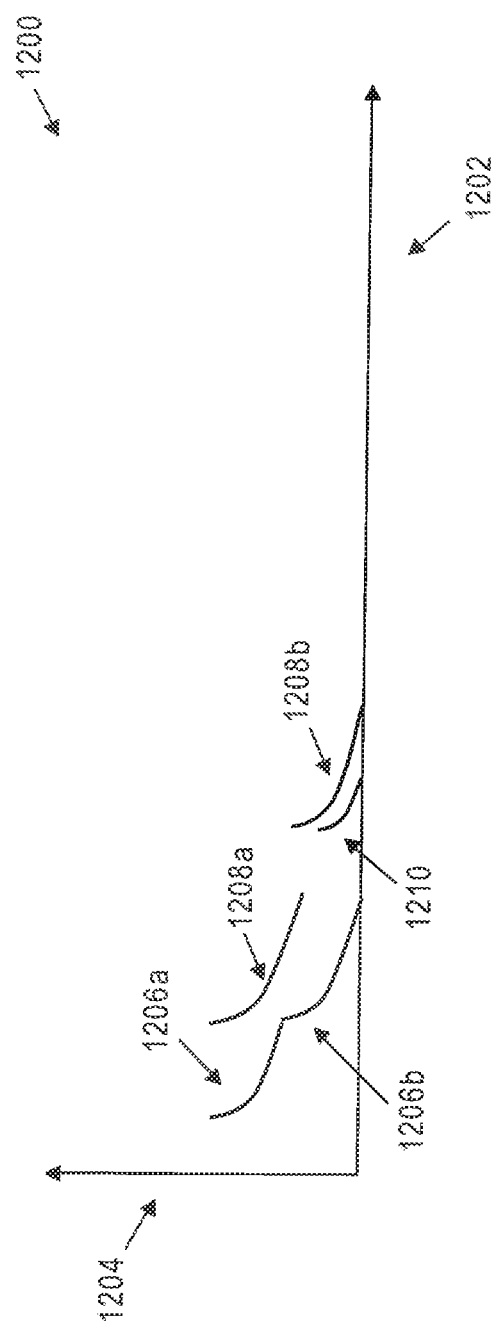
FIG. 12 illustrates an embodiment of a graphical illustration of residual charges of the discharge sequence shown in FIG. 11.

FIG. 12 illustrates an embodiment of a graphical illustration 1200 of residual charges 1206a-b, 1208a-b, 1210 of the MP therapy/discharge sequence 1100, in FIG. 11. The residual charges 1206a-b, 1208a-b, 1210 are plotted with a horizontal axes 1202 representing time and a vertical axis 1204 representing a voltage across the coupling capacitors 324. For example, the residual charges 1206a-b represents the voltage across the coupling capacitor 324 from the first pulse 503. A decrease in the residual charge 1206a is based on the discharge pulse 1112a. For example, during the PP interval 1122 the one or more processors instruct the switch 226 to close the discharge switch 316. The discharge pulse 1112a extends for the length of the PP interval 1122, however, the residual charge 1206a remains above the predetermined threshold. For example, the one or more processors compare the residual charge 1206a with the predetermined threshold, and determines that the residual charge 1206a is above the predetermined threshold.

The residual charge 1208a represents the voltage across the coupling capacitor 324 from the second pulse 1104. The residual charge 1206b represents the remaining voltage across the coupling capacitor 324 from the first pulse 1103. The one or more processors instruct the switch 226 to close the discharge switches 316 for the LV electrodes of the first and second pulses 1103-1104. The discharge switches 316 of the switch 226 may be closed concurrently and/or simultaneously with respect to each other. The discharge pulses 1112b, 1114a occur during the PP interval 1124. As the discharge switches 316 are closed, the residual charges 1206b, 1208a decrease. The discharge pulses 1112b, 1114a extend for a duration of the PP interval 1124. At the end of the PP interval 1120, the one or more processors determine that the residual charge 1206b is at the predetermined threshold. For example, the one or more processors determine that the coupling capacitor 324 for the LV electrodes of the first pulse 1103 is depleted. Additionally or alternatively, the one or more processors determine that the residual charge 1208a is above the predetermined threshold. For example, the one or more processors determine that the coupling capacitor 324 for the LV electrodes of the second pulse 1104 is not depleted.

During the PP interval 1126, the one or more processors instruct the switch 226 to close the discharge switches 316 associated with the LV electrode of the second pulse 1104 and the RV electrode of the third pulse 1105. The discharge switches 316 of the switch 226 may be closed concurrently and/or simultaneously with respect to each other. The discharge pulses 1116, 1114b occur during the PP interval 1126.

As the discharge switches 316 are closed, the residual charges 1208b, 1210 decrease. The discharge pulses 1116, 1114b extend for a duration of the PP interval 1126. At the end of the PP interval 1126, the one or more processors determine that the residual charges 1208b, 1210 are at the predetermined threshold. For example, the one or more processors compare the residual charges 1208b, 1210 with the predetermined threshold. The one or more processors determine that residual charges 1208b, 1210 are at the predetermined threshold, and the coupling capacitors 324 are depleted and opens the discharge switch 316.

The one or more processors select one of the MPP therapy/discharge sequences 500, 700, 900, 1100 based on the lengths of the PP intervals of the first cardiac cycle.

For example, the one or more processors identify a duration of the PP intervals defining the first cardiac cycle. The one or more processors determine a duration of the PP interval 522, 722, 922, 1122 of the first cardiac cycle. For example, the one or more processors determine that a duration between the first and second pulses 503-504, 703-704, 903-904, 1103-1104 is 8 milliseconds. Based on the duration of the PP interval, the one or more processors determine that multiple discharge pulses 512a-b, 712a-b, 912a-b, 1112a-b are needed. For example, the one or more processors determine that multiple discharge pulses 512a-b, 712a-b, 912a-b, 1112a-b are needed to deplete the voltage on the coupling capacitor 324 based on the first pulse 503, 703, 903, 1103. The one or more processors determine a duration between the second and third pulses 504-505, 704-705, 904-905, 1104-1105. The duration of the PP interval 524, 724, 924, 1124 can be utilized by the one or more processors to select one of the MPP therapy/discharge sequences 500, 700, 900, 1100.

For example, the one or more processors determine that the duration between the second and third pulses 504-505, 704-705, 904-905, 1104-1105 is 16 milliseconds. Based on the duration, the one or more processors determine that a single discharge pulse (e.g., the discharge pulse 514, 714, 914, 1114) can be positioned within the PP interval 524, 724, 924, 1124 to discharge all of the residual charge associated with the second pulse 503, 703, 903, 1103. The one or more processors narrow the possible discharge sequences to the MPP therapy/discharge sequences 500 and 900.

In another example, the one or more processors determine that the duration between the second and third pulses 504-505, 704-705, 904-905, 1104-1105 is 8 milliseconds. Based on the duration of the PP interval 524, 724, 924, 1124, the one or more processors determine that a portion of a discharge pulse can be positioned within the PP interval 524, 724, 924, 1124. The one or more processors narrow the possible MPP therapy/discharge sequences to the MPP therapy/discharge sequence 1100.

In another example, the one or more processors determine that the duration between the second and third pulses 504-505, 704-705, 904-905, 1104-1105 is 30 milliseconds. Based on the duration of the PP interval 524, 724, 924, 1124, the one or more processors determine that multiple discharge pulses can be positioned within the PP interval 524, 724, 924, 1124. For example, the one or more processors narrow the possible MPP therapy/discharge sequences to the MPP therapy/discharge sequence 700.

Based on the duration between the second and third pulses 504-505, 704-705, 904-905, 1104-1105, the one or more processors can narrow to a single discharge sequence. For example, the duration between the second and third pulses 504-505, 704-705, 904-905, 1104-1105 is 16 milliseconds. The one or more processors narrow the discharge sequences to the discharge sequences 500 and 900. The PP interval 526, 726, 926, 1126 after the third pulse 505, 705, 905, 1105 is based on a second cardiac cycle. For example, the duration is based between the third pulse 505, 705, 905, 1105 and the A pulse 502, 702, 902, 1102 of the second cardiac cycle. Based on the duration, the one or more processors can select one of the MPP therapy/discharge sequences 500, 900.

For example, the duration from the third pulse 505, 705, 905, 1105 and the A pulse 502, 702, 902, 1102 of the second cardiac cycle is 25 milliseconds. Based on the duration, the one or more processors determine that partial and full discharge pulses (e.g., the discharge pulse 512b, the discharge pulse 516) can be positioned subsequent to the third pulse 505, 705, 905, 1105. The one or more processors select the MPP therapy/discharge sequence 500.

In another example, the duration from the third pulse 505, 705, 905, 1105 and the A pulse 502, 702, 902, 1102 of the second cardiac cycle is 16 milliseconds. Based on the duration, the one or more processors determine that two partial discharge pulses (e.g., the discharge pulses 912b, 916) can be positioned subsequent to the third pulse 505, 705, 905, 1105. The one or more processors select the MPP therapy/discharge sequence 900.

Closing Statements

It should be clearly understood that the various arrangements and processes broadly described and illustrated with respect to the Figures, and/or one or more individual components or elements of such arrangements and/or one or more process operations associated of such processes, can be employed independently from or together with one or more other components, elements and/or process operations described and illustrated herein. Accordingly, while various arrangements and processes are broadly contemplated, described and illustrated herein, it should be understood that they are provided merely in illustrative and non-restrictive fashion, and furthermore can be regarded as but mere examples of possible working environments in which one or more arrangements or processes may function or operate.

As will be appreciated by one skilled in the art, various aspects may be embodied as a system, method or computer (device) program product. Accordingly, aspects may take the form of an entirely hardware embodiment or an embodiment including hardware and software that may all generally be referred to herein as a "circuit," "module" or "system." Furthermore, aspects may take the form of a computer (device) program product embodied in one or more computer (device) readable storage medium(s) having computer (device) readable program code embodied thereon.

Any combination of one or more non-signal computer (device) readable medium(s) may be utilized. The non-signal medium may be a storage medium. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a dynamic random access memory (DRAM), a read-only memory (ROM), an erasable programmable read-only memory (EPROM or Flash memory), a portable compact disc read-only memory (CD-ROM), an optical storage device, a magnetic storage device, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of network, including a local area network (LAN) or a wide area network (WAN), or the connection may be made through other devices (for example, through the Internet using an Internet Service Provider) or through a hard wire connection, such as over a USB connection. For example, a server having a first processor, a network interface, and a storage device for storing code may store the program code for carrying out the operations and provide this code through its network interface via a network to a second device having a second processor for execution of the code on the second device.

Aspects are described herein with reference to the Figures, which illustrate example methods, devices and program products according to various example embodiments. These program instructions may be provided to a processor of a general purpose computer, special purpose computer, or other programmable data processing device or information handling device to produce a machine, such that the instructions, which execute via a processor of the device implement the functions/acts specified. The program instructions may also be stored in a device readable medium that can direct a device to function in a particular manner, such that the instructions stored in the device readable medium produce an article of manufacture including instructions which implement the function/act specified. The program instructions may also be loaded onto a device to cause a series of operational steps to be performed on the device to produce a device implemented process such that the instructions which execute on the device provide processes for implementing the functions/acts specified.

The units/modules/applications herein may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the modules/controllers herein may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The units/modules/applications herein may execute a set of instructions that are stored in one or more storage elements, in order to process data. The storage elements may also store data or other information as desired or needed. The storage element may be in the form of an information source or a physical memory element within the modules/controllers herein. The set of instructions may include various commands that instruct the modules/applications herein to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings herein without departing from its scope. While the dimensions, types of materials and coatings described herein are intended to define various parameters, they are by no means limiting and are illustrative in nature. Many other embodiments will be apparent to those of skill in the art upon reviewing the above description. The scope of the embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects or order of execution on their acts.

What is claimed is:

1. A method for managing residual charge in connection with multi-point pacing (MPP), the method comprising:
   providing an electrode configuration that includes an atrial (A) electrode, a right ventricular (RV) electrode and multiple left ventricular (LV) electrodes;
   delivering pacing pulses for an MPP therapy, during a first cardiac cycle, from a pulse generator to the electrode configurations, the pacing pulses separated by pacing pulse (PP) intervals;
   dynamically adjusting at least one of a timing or a duration of discharge pulses for the residual charge to form a discharge sequence; and
   activating the discharge pulses based on the discharge sequence, during the first cardiac cycle, to the multiple LV electrodes to distribute the residual charge across the PP intervals.

2. The method of claim 1, wherein the dynamically adjusting operation includes determining a discharge sequence based on lengths of first and second PP intervals.

3. The method of claim 1, wherein the dynamically adjusting operation includes selecting a discharge sequence that reduces a portion of the residual charge associated with a first pacing pulse after at least first, second, and third pacing pulses.

4. The method of claim 1, wherein the discharge sequence includes at least first and second discharge pulses for the residual charge associated with a first pacing pulse, the at least first and second discharge pulses are activated during corresponding first and second PP intervals.

5. The method of claim 1, wherein the delivering operation comprise delivering first and second pacing pulses utilizing first and second LV electrodes and wherein the discharge sequence includes at least first and second discharge pulses for the residual charge associated with the first pacing pulse, the at least first and second discharge pulses are activated after the first and second pacing pulses.

6. The method of claim 1, wherein the discharge sequence includes at least one of a single discharge pulse, two discharge pulses, or simultaneous discharge pulses.

7. The method of claim 1, further comprising calculating lengths of first, second, and third PP intervals based on the first cardiac cycle of a patient, wherein the first, second, and third PP intervals are interposed between the first, second, and third pulses, respectively, and wherein the at least one of the timing or the duration of the discharge pulses is dynamically adjusted based on the length of at least one of the first, second or third PP intervals.

8. A system for managing residual change in connection with multi-point pacing (MPP), the system comprising:
electrodes configured to be located proximate to an atrial (A) site, a right ventricular (RV) site and multiple left ventricular (LV) sites of the heart;
a pulse generator to generate pacing pulses;
switch;
memory to store program instructions;
one or more processors configured to implement the program instructions to:
deliver pacing pulses for an MPP therapy, during a first cardiac cycle, from the pulse generator to the electrode configurations the pacing pulses separated by pacing pulse (PP) intervals;
dynamically adjust at least one of a timing or a duration of discharge pulses for the residual charge to form a discharge sequence; and
control the switch to activate the discharge pulses based on the discharge sequence, during the first cardiac cycle, to the multiple LV electrodes to distribute the residual charge across the PP intervals.

9. The system of claim 8, wherein the one or more processors are configured to determine a discharge sequence based on lengths of first and second PP intervals.

10. The system of claim 8, wherein the one or more processors are configured to select a discharge sequence that reduces a portion of the residual charge associated with a first pacing pulse after at least first, second and third pacing pulses.

11. The system of claim 8, wherein the discharge sequence includes at least first and second discharge pulses for the residual charge associated with a first pacing pulse, the at least first and second discharge pulses are activated during corresponding first and second PP intervals.

12. The system of claim 8, wherein the one or more processors is configured to deliver first and second pacing pulses utilizing first and second LV electrodes.

13. The system of claim 12, wherein the discharge sequence includes at least first and second discharge pulses for the residual charge associated with the first pacing pulse, the at least first and second discharge pulses are activated after the first and second pacing pulses, respectively.

14. The system of claim 8, wherein the discharge sequence includes a least one of a single discharge pulse, two discharge pulses, or simultaneous discharge pulses.

15. The system of claim 8, wherein the one or more processors are configured to calculate lengths of first, second, and third PP intervals based on the first cardiac cycle of a patient, wherein the first, second, and third PP intervals are interposed between the first, second, and third pulses, respectively, and wherein the at least one of the timing or the duration of the discharge pulses is dynamically adjusted based on the length of at least one of the first, second or third PP intervals.

16. A method for managing residual charge in connection with multi-point pacing (MPP), the method comprising:
providing an electrode configuration that includes an atrial (A) electrode, a right ventricular (RV) electrode and multiple left ventricular (LV) electrodes;
delivering pacing pulses for an MPP therapy, during a first cardiac cycle, from a pulse generator to the electrode configurations, the pacing pulses separated by pacing pulse (PP) intervals;
calculating a length of first, second, and third PP intervals based on a cardiac cycle of a patient, wherein the first, second, and third PP intervals are interposed between the first, second, and third pulses, respectively;
dynamically adjusting at least one of a timing or a duration of discharge pulses for the residual charge to form a discharge sequence based on lengths of the first and second PP intervals, wherein the discharge sequence includes at least one of a single discharge pulse, two discharge pulses, or simultaneous discharge pulses; and
activating the discharge pulses based on, the discharge sequence, during the fir cardiac, cycle, to the multiple LV electrodes to distribute the residual charge across the PP intervals.

17. The method of claim 16 wherein the dynamically adjusting operation includes selecting a discharge sequence that reduces a portion of the residual charge associated with a first pacing pulse after at least first, second and third pacing pulses.

18. The method of claim 16 wherein the discharge sequence includes at least first and second discharge pulses for the residual charge associated with a first pacing pulse, the at least first and second discharge pulses activated during corresponding first and second PP intervals.

19. The method of claim 16, wherein the delivering operation comprises delivering first and second pacing pulses utilizing the first and second LV electrodes.

20. The method of claim 19, wherein the discharge sequence includes at least first and second discharge pulses for the residual charge associated with the first pacing pulse, the at least first and second discharge pulses are activated after the first and second pacing pulses.

* * * * *